US009937198B2

(12) United States Patent
Zhang et al.

(10) Patent No.: US 9,937,198 B2
(45) Date of Patent: Apr. 10, 2018

(54) MULTI-FUNCTIONAL COMPOSITION AND PREPARATION METHOD AND APPLICATION THEREOF

(71) Applicants: Suzhou Sciscape Bio-Pharmaceutical Technology Co., Ltd., Jiangsu (CN); Pinghu Sciscape Bio-Pharmaceutical Technology Co., Ltd., Zhejiang (CN); Beijing Bailening Biotechnology Co. Ltd., Beijing (CN)

(72) Inventors: Chenggang Zhang, Zhejiang (CN); Zhihui Li, Beijing (CN); Yu Li, Jiangsu (CN)

(73) Assignees: Pinghu Sciscape Bio-Pharmaceutical Technology Co., Ltd., Zhejiang (CN); Beijing Bailening Biotechnology Co., Ltd., Beijing (CN); Suzhou Sciscape Bio-Pharmaceutical Technology Co. Ltd., Jiangsu (CN)

( * ) Notice: Subject to any disclaimer, the term of this patent is extended or adjusted under 35 U.S.C. 154(b) by 0 days.

(21) Appl. No.: 14/894,209

(22) PCT Filed: May 30, 2014

(86) PCT No.: PCT/CN2014/078886
§ 371 (c)(1),
(2) Date: Nov. 25, 2015

(87) PCT Pub. No.: WO2014/190935
PCT Pub. Date: Dec. 4, 2014

(65) Prior Publication Data
US 2016/0129037 A1  May 12, 2016

(30) Foreign Application Priority Data

May 30, 2013 (CN) .......................... 2013 1 0207729
May 30, 2013 (CN) .......................... 2013 1 0207747
May 30, 2013 (CN) .......................... 2013 1 0207750
May 30, 2013 (CN) .......................... 2013 1 0207752
May 30, 2013 (CN) .......................... 2013 1 0207755
May 30, 2013 (CN) .......................... 2013 1 0208130
May 30, 2013 (CN) .......................... 2013 1 0208145
May 30, 2013 (CN) .......................... 2013 1 0208165
May 30, 2013 (CN) .......................... 2013 1 0208184

(51) Int. Cl.
A61K 31/715 (2006.01)
A61K 31/7036 (2006.01)
A61K 31/7056 (2006.01)
A61K 31/734 (2006.01)
A61K 31/7016 (2006.01)
A61K 31/4196 (2006.01)
A61K 36/02 (2006.01)
A23L 2/52 (2006.01)
A61K 8/49 (2006.01)
A61K 8/60 (2006.01)
(Continued)

(52) U.S. Cl.
CPC .............. A61K 31/715 (2013.01); A23L 2/39 (2013.01); A23L 2/52 (2013.01); A23L 17/60 (2016.08); A23L 29/30 (2016.08); A23L 33/10 (2016.08); A23L 33/105 (2016.08); A61K 8/496 (2013.01); A61K 8/60 (2013.01); A61K 8/602 (2013.01); A61K 8/733 (2013.01); A61K 8/9706 (2017.08); A61K 9/0095 (2013.01); A61K 31/4196 (2013.01); A61K 31/70 (2013.01); A61K 31/7016 (2013.01); A61K 31/7036 (2013.01); A61K 31/7056 (2013.01); A61K 31/734 (2013.01); A61K 36/02 (2013.01); A61K 47/12 (2013.01); A61K 47/26 (2013.01); A61K 47/46 (2013.01); A61Q 19/00 (2013.01); A61Q 19/06 (2013.01); A23V 2002/00 (2013.01); A61K 2800/782 (2013.01)

(58) Field of Classification Search
CPC .............. A61K 31/715; A61K 31/7016; A61K 31/7036; A61K 31/4196; A61K 31/7056; A61K 31/734; A61K 36/02; A23L 1/30; A23V 2002/00
USPC ......................................... 514/35, 43, 53, 54
See application file for complete search history.

(56) References Cited

U.S. PATENT DOCUMENTS 5,091,524 A   2/1992  Vertesy et al.
5,354,685 A  10/1994  Murao et al.
(Continued)

FOREIGN PATENT DOCUMENTS

CN   1106065    8/1995
CN   1461656   12/2003
(Continued)

OTHER PUBLICATIONS

Yang, Yan et al., "Trehalase inhibitor—new pesticide leading structure" Chemistry of Life, vol. 03, No. 25, Mar. 31, 2005 (Mar. 31, 2005), pp. 196-198 (no translation provided).
(Continued)

Primary Examiner — Yih-Horng Shiao
(74) Attorney, Agent, or Firm — Duane Morris LLP

(57) ABSTRACT

A multi-functional composition is disclosed as well as the preparation method and applications thereof. The composition contains a marine algae-derived material and an enzyme inhibitor. The marine algae-derived material is one from the group consisting of natural algal saccharide, alginic acid and alginate or is a mixture of several of them. The enzyme inhibitor is an inhibitor to the enzyme decomposing the material derived from marine algae.

10 Claims, 1 Drawing Sheet

(51) Int. Cl.

| | | |
|---|---|---|
| A61K 8/73 | (2006.01) | |
| A61Q 19/00 | (2006.01) | |
| A61K 47/12 | (2006.01) | |
| A61K 9/00 | (2006.01) | |
| A61K 47/26 | (2006.01) | |
| A61K 47/46 | (2006.01) | |
| A61K 31/70 | (2006.01) | |
| A23L 2/39 | (2006.01) | |
| A61Q 19/06 | (2006.01) | |
| A23L 29/30 | (2016.01) | |
| A23L 33/10 | (2016.01) | |
| A23L 33/105 | (2016.01) | |
| A23L 17/60 | (2016.01) | |
| A61K 8/9706 | (2017.01) | |

(56) References Cited

U.S. PATENT DOCUMENTS

| | | | |
|---|---|---|---|
| 5,494,812 A | 2/1996 | Murao et al. | |
| 2006/0188627 A1 | 8/2006 | Brouns et al. | |
| 2007/0254848 A1* | 11/2007 | Geng | C07H 3/06 514/35 |
| 2009/0304664 A1* | 12/2009 | Lindquist | A61K 38/1709 514/1.1 |
| 2011/0098245 A1 | 4/2011 | Suzuki et al. | |
| 2015/0025028 A1 | 1/2015 | Lee-Chen | |

FOREIGN PATENT DOCUMENTS

| | | |
|---|---|---|
| EP | 0784095 A2 | 7/1997 |
| JP | 02-196780 A | 8/1990 |
| JP | 03-172155 A | 7/1991 |
| JP | 05-186353 A | 7/1993 |
| JP | 05-279374 A | 10/1993 |
| JP | 09-208475 A | 8/1997 |
| JP | 10-017478 A | 1/1998 |
| JP | 11-158075 A | 6/1999 |
| JP | 2000-198736 A | 7/2000 |
| JP | 2006-206474 A | 8/2006 |
| WO | 97/06676 | 2/1997 |
| WO | 00/55349 A1 | 9/2000 |
| WO | 2011/108762 A1 | 9/2011 |
| WO | WO 2013/038197 * | 3/2013 |

OTHER PUBLICATIONS

International Search Report dated Oct. 10, 2014 for PCT/CN2014/078886.
Substantive Examination Report dated Jan. 27, 2016 for corresponding GB Application No. GB1521138.6.
English Translation of International Preliminary Report on Patentability dated Dec. 18, 2015 for PCT/CN2014/078886.
Hwang, Y., paper entitled, "Functional expression of human trehalase in Escherichia coli and identification of novel trehalase inhibitors", Jan. 1, 2013, Dean of Life Sciences Institute, Taiwan Normal University, obtained from the Internet at URL <http://www.airitilibrary.com/Publication/alDetailedMesh?docid=U0021-0801201418030541>.
Editorial Hot Topic: The Medicinal Chemistry of Glycosidase Inhibitors (Guest Editors: Seiichiro Ogawa and Hideya Yuasa),Current Topics in Medicinal Chemistry, 2009, vol. 9, No. 1, pp. 1-2.
Office Action issued in connection with corresponding Korean patent application No. 10-2015-7037026, dated Aug. 22, 2017, 8 pages.
Extended European Search Report issued for European patent application No. 14803865.6, dated Dec. 9, 2016, 7 pages.
Office Action issued for Japanese patent application No. 2016-515642, dated Dec. 21, 2016, 4 pages.
Office Action issued for Japanese patent application No. 2016-515642, dated Apr. 26, 2017, 2 pages.
Examination Report issued for GB patent application No. GB1521138.6, dated Jan. 27, 2016, 3 pages.
Examination Report issued for GB patent application No. GB1521138.6, dated Jun. 16, 2016, 4 pages.
Examination Report issued for GB patent application No. GB1521138.6, dated Apr. 26, 2017, 4 pages.
Kim CJ et al: "Overproduction of trehalose by metabolically engineered Escherichia coli in the presence of trehalase inhibitor, validamycin a under osmotic stress", New Biotechnology, Elsevier BV, NL, vol. 25, Sep. 1, 2009 (Sep. 1, 2009), pp. S326-S327,XP026461756.
He Li et al: "Enhanced production of trehalose inby homologous expression ofin the presence of the trehalase inhibitor, validamycin A, at high osmolarity", Journal of Bioscience and Bioengineering, Elsevier, Amsterdam, NL, vol. 113, No. 2, Sep. 24, 2011 (Sep. 24, 2011), pp. 224-232, XP028454985.
Asano N: "GL Ycosidase Inhibitors: Update and Perspectives on Practical Use", Glycobiology, Oxford University Press, US, vol. 13, No. 10, Oct. 1, 2003 (Oct. 1, 2003), pp. 93R-104R, XP008031797.
A.B Richards et al: "Trehalose: a review of properties, history of use and human tolerance, and results of multiple safety studies", Food and Chemical Toxicology., vol. 40, No. 7, Jul. 1, 2002 (Jul. 1, 2002), pp. 871-898, XP055323984.

* cited by examiner

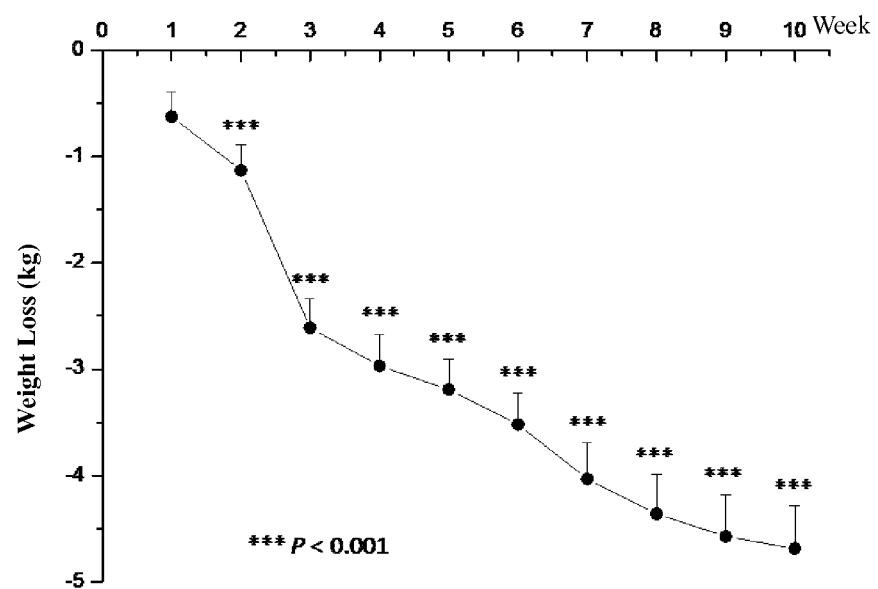

MULTI-FUNCTIONAL COMPOSITION AND PREPARATION METHOD AND APPLICATION THEREOF

CROSS REFERENCE TO RELATED APPLICATIONS

This application is a U.S. national phase application filed under 35 U.S.C. § 371 of International Application No. PCT/CN2014/078886, which was filed May 30, 2014, and which claims the benefit of the filing dates of Chinese Patent Application Nos. 201310207729.1, filed on May 30, 2013, 201310207747.X, filed on May 30, 2013, 201310207750.1, filed on May 30, 2013, 201310207755.4, filed on May 30, 2013, 201310208184.6, filed on May 30, 2013, 201310208165.3, filed on May 30, 2013, 201310208145.6, filed on May 30, 2013, 201310208130.X, filed on May 30, 2013, and 201310207752.0, filed on May 30, 2013.

FIELD OF THE INVENTION

The present invention relates to the field of functional products, medicine and health care, particularly to a multi-functional composition and its preparation method and application.

BACKGROUND OF THE INVENTION

Marine algae, a general term for algae in marine, are usually attached to the seabed or some solid constructions. They are simple individual plants or a long string of plants composed of basic cells. They are aquatic plants with the stalks or leaves hard to be recognized when appearing in large quantities. The organisms by the name of marine algae include numerous species. They differ greatly in shapes and belong to many biological species. What they have in common is that they live in the seawater and can synthesize organics by photosynthesis with the pigments in their bodies. The most common large marine algae are seaweeds such as green algae, red algae and brown algae. Marine algae often grow densely in an expanse in shallow water and form obvious zones on the coast where the water is less than 50 meters in depth. The marine algae growing above high-water line are often exposed to the air. On the other hand, the marine algae growing below the low-water line cannot be exposed in the air for a long time and thus cannot grow near the shore, which are, for example, the populations from the genera *Fucus*, *Macrocystis*, *Nereocystis* and *Laminaria*. They can only reproduce below 18° C. and are distributed only in cold water areas.

With the advancement of science and technology, people get increasing understandings on the application value of marine algae in industry and life. Due to extensive sources, low price and other advantages, the extracts from marine algae have become the focus in various fields. The extracts are, for instance, trehalose, algal polysaccharides, alginic acid and the inorganic salts thereof.

The trehalose is a non-reducing saccharide formed by two glucose molecules with a 1,1-glucosidic bond. It has three isomers, i.e., trehalose (α, α), isotrehalose (β, β) and neotrehalose (α, β). The trehalose commercially available in the market is typically the mixture of these three isomers, mostly trehalose (α, α). Trehalose is widely precent in many animals, plants and microorganisms in nature that can be used as food. For instance, the content of trehalose is relatively high in mushrooms, marine algae, beans, shrimps, bread, beer and yeast-fermented food that commonly appear in popelpe's daily life. The trehalose is most commonly used as the natural edible sweetener.

Also, the trehalose has a miraculous protective effect on living bodies because such a compound can form a unique protective film on the cell surface under harsh environmental conditions with a very high temperature, a very low temperature, a high osmotic pressure, a dry condition with water loss and the like. In particular, the trehalose effectively protects protein molecules from denaturation and deactivation, maintaining the life process and biological characteristics of living bodies. The extraordinary resistance to external harsh environment in many species directly relates to a large amount of trehaloses in their bodies. Such a unique functional feature enables trehalose to become an important ingredient in cosmetics maintaining cell viability and preserving moisture and also become a good activity protector for proteins, enzymes, vaccines and other biological products. Moreover, it may also function as a unique food ingredient which can prevent food degradation, preserve the fresh flavor of food and improve food quality. This feature has greatly expanded the application of this compound. Similar to trehalose, algal polysaccharides are all safe and reliable natural saccharides from marine algae.

The alginic acid is a powder of light yellow and almost odorless. It is a polysaccharide generated from linear polymerization of monosaccharide-derived uronic acidanda. Alginic acid is mainly originated from brown algae such as kelp, gulf weed, yellow tang and giant kelp. At present, alginic acid is used in the adhesive agents and disintegrating agents in the pharmaceutical field. Sodium alginate, calcium alginate and potassium alginate which are the inorganic salts of alginic acid are similar to alginic acid in nature.

It is a task for the professionals to explore more fields where the resourceful algae extracts can be applied.

SUMMARY OF THE INVENTION

The main objective of the present invention is to introduce special applications of marine algae extracts in several new fields and to provide a multi-functional composition on this basis. The composition contains a marine algae-derived material and an enzyme inhibitor, wherein the mass percentage of the enzyme inhibitor in the multi-functional composition is no lower than 0.001%, the marine algae-derived material is one or more from the group consisting of natural algal saccharide, alginic acid and alginate, and the enzyme inhibitor is an inhibitor to the enzyme which decomposes the marine algae-derived material.

The natural algal saccharide is either trehalose or algal polysaccharide or their mixture. The aquo compound and the isomer of the natural algal saccharide are also included.

The enzyme inhibitor is one or more from the group consisting of validamycin, hexaconazole, trehazolin, 2R, 5R-dimethylol-3R, 4R-dihydroxy pyrrole, trehalostatin, Salbostatin, Suidatrestin and MDL25637.

The alginate includes one or more from the group consisting of sodium alginate, potassium alginate and calcium alginate.

Another objective of the present invention is to provide a method for preparing this multi-functional composition. The multi-functional composition is a powder composition prepared by directly mixing the powdery marine algae-derived material and the enzyme inhibitor evenly.

The multi-functional composition is a liquid composition prepared by mixing the solution of marine algae-derived material and the solution of the enzyme inhibitor or by dissolving the powder composition.

Another objective of the present invention is to provide the use of the multi-functional composition in the preparation of a multi-functional product.

The multi-functional product includes, but not limited to, a sugar substitute product for diabetics, a product for decreasing blood sugar, a product for defaecation and gut purge, a sliming product, a beauty product, a product for ameliorating osteoporosis, a product for improving sleeping, a product for ameliorating menstrual disorder and an anti-fatigue product, or a mixed product simultaneously exerting at least two of the above mentioned functions.

The multi-functional product is a health-care product or a medicine containing the multi-functional composition above with the multi-functional composition being an active ingredient for the health-care product or the medicine.

The health-care product or the medicine is in a form of pill, capsule, powder, granule or oral liquid.

The product may also be a functional food containing the composition.

The functional food is in a form of lozenge, solid beverage or liquid beverage.

The multi-functional composition provided in the present invention is of wide resources and low price. It can be made from the marine algae and has no toxicity and side effects to human body. The production process for making it a product in various oral forms is simple. Further, experiments have shown that the multi-functional product made of the composition of the present invention has efficacies of reducing blood glucose, relaxing the bowels and purging the gut, reducing weight, maintaining beauty and keeping young, ameliorating osteoporosis, improving sleeping, ameliorating menstrual disorder and resisting fatigue and may be used to treat and alleviate diabetes, constipation, abdominal distension and abdominal pain induced by constipation, obesity, calcium deficiency, insomnia and menstrual disorder. The multi-functional product produces effect quickly, acts gently, has an obvious dose-effect relationship and provides no toxicity and side effects. The multi-functional product may be formulated in multiple oral forms for the convenient administration in patients and is thus a safe and reliable multi-functional product for patients.

BRIEF DESCRIPTION OF THE DRAWINGS

FIG. 1 shows the average body weight changes in volunteers participating in the sliming experiment.

DETAILED DESCRIPTION OF THE EMBODIMENTS

The marine algae based material is universally present in our daily food. The trehalose or the algal polysaccharides in marine algae-derived material may also be used as a safe and reliable natural sugar to spice up the food. No matter which form is adopted, its content in food is very small and also limited amount is intaken by human body. Nevertheless, the inventors have analyzed its changes in human body. It has been found that after the marine algae-derived material is taken into human body, it will be decomposed into glucoses under the action of enzymes (enzymes decomposing the marine algae-derived material) in stomach and intestinal tract which are absorbed by human body through intestinal tract. As only a little amount of marine algae-derived material is contained in the food, the changes of the marine algae-derived material in human body are often overlooked.

Based on the above research, the inventors wondered what would happen if the marine algae-derived material has not been decomposed in the stomach and intestine and what factors may prevent it from being decomposed. As a result, they found that after the marin algae-derived material was combined with the inhibitor to the enzyme (the enzyme decomposing the marine algae-derived material) and then administered to human body, the enzyme inhibitor was bonded with said enzymes in stomach and intestine at first to keep the marine algae-derived material from being decomposed so that the marine algae-derived material might enter the intestinal tract in its original form (rather than the glucose form after it was decomposed). Also, they found that the undecomposed marine algae-derived material in the intestinal tract indeed created magical changes in human body. For example, the composition was found to have unexpected efficacies such as effects on reducing blood glucose, relaxing the bowels and purging the gut, losing weight, maintaining beauty and keeping young, ameliorating osteoporosis, improving sleeping, ameliorating menstrual disorder and resisting fatigue. The inventors further confirmed these miraculous efficacies through experiments.

Thereby, the present invention first provides a multi-functional composition which contains a marine algae-derived material and an enzyme inhibitor. The percentage by mass of the enzyme inhibitor in the composition is no lower than 0.001%.

The marine algae-derived material useful in the present invention includes trehalose, algal polysaccharides, alginic acid and the inorganic salt thereof such as sodium alginate, calcium alginate and potassium alginate. The foresaid marine algae-derived material with or without crystal water in the present invention may both be used. In the present invention, a single kind of the marine algae-derived materials listed above may be used, or several of them may be used in combination at any ratio therebetween or thereamong.

A lot of enzyme inhibitors may be used in the present invention, including the already known validamycin, hexaconazole, trehazolin, 2R,5R-dimethylol,3R,4R-dihydroxy pyrrole (DMDP), trehalostatin, Salbostatin, Suidatrestin, Trehalin or MDL25637 or the combination of several of them, or the analogues of these substances and the mixture thereof, or an object (including the microorganism and the plant) that can be directly applied and is capable of generating said substances such as *Streptomyces hygroscopicus* capable of generating validamycin or an organism capable of generating hexaconazole.

In particular, validamycin, having eight isomers (isomers A to H), is a compound generated by *Actinomycetes* and is a bactericidal antibiotic with certain selectivity. It can be easily absorbed by bacteria and quickly transmitted inside the cells, inhibiting certain enzymes to affect the metabolism of saccharides in bacteria and further to interfere and inhibit the growth and development of bacteria. The mixture of water soluble glucosides generated by *Streptomyces hygroscopicus* var. *jinggangensis* has the highest activity to *Pellicularia sasakii*. Among the validamycin isomers, the pure validamycin A is a white powder and does not have a fixed melting point. It is softened at 95 to 100° C. and decomposed at 130 to 135° C. Further, it is soluble in water. Validamycin A has an acute oral toxicity ($LD_{50}$) in rats that is above 20 g/kg while providing no toxicity to bees and other beneficial insects. In particular, validamycin A can be easily absorbed by bacteria and transmitted inside the cells, disturbing and inhibiting normal growth and development of bacteria so as to play its role in treatment. In the present invention, one isomer or a mixture of several isomers may be used. The commercially purchased validamycin related product mainly contains validamycin A. Hexaconazole is a systemic agent and can effectively prevent and treat the diseases induced by Ascomycotina, Basidiomycotina and Deuteromycotina. Especially, it plays a good role in preventing and treating the diseases induced by Basidiomycotina and Ascomycotina such as powdery mildew, rust disease, scab of cucurbi, brown spot, anthracnose, sheath blight and rice false smut. On the other hand, trehazolin has insecticidal and antifungal activity and is a highly specific inhibitor to trehalase. Also, the validamycin, hexaconazole and trehazolin are all enzyme inhibitors and are currently used in the prevention and treatment of rice sheath blight disease, rice false smut, wheat sharp eyespot, seedling blight of cotton, *ginseng*, bean and melon, and core northern leaf blight and core southern leaf blight. In addition, they are also helpful in preventing and controlling harmful insects such as locust.

The marine algae-derived material and the enzyme inhibitor mentioned above are all commercially available.

In the present invention, the powdery marine algae-derived material and the enzyme inhibitor may be directly mixed evenly to form a powder composition, or the solution of marine algae-derived material and the solution of the enzyme inhibitor are mixed to form a liquid composition. Alternatively, the powder composition is dissolved to provide a liquid composition. Further, the powder composition or the liquid composition may be made into health-care products or medicines in the form of pill, powder, granule, capsule or oral liquid by conventional methods and may also be made into functional foods in the form of lozenge, solid beverage or liquid beverage.

The multi-functional composition in the present invention is provided to humans as an additive functional product. The human body will be additionally given the marine algae-derived material upon administration. In the meanwhile, the marine algae-derived material will not be decomposed by the enzymes due to the presence of the enzyme inhibitor and will maintain its undecomposed form in the intestinal tract so as to exert special health-care and medical functions in human body.

Hereinafter, the present invention will be further described and illustrated in detail with reference to specific examples, but these examples will by no means limit the present invention. Any modification made by those skilled in the art to the examples of the present invention under the teachings of this specification shall fall within the scope as defined in the claims of the present invention.

The biological materials used in the examples are obtained from a wide range of sources, and all the biological materials available without violating the law and ethics may be exchangeably used as indicated in the examples. Unless otherwise indicated, all the methods employed here are conventional ones. Also, unless otherwise stated, the materials or reagents with the same name are substantially the same throughout the examples.

Example 1: Multi-Functional Composition in the Present Invention

Raw materials were weighed respectively according to the proportion by weight of the marine algae-derived material and the enzyme inhibitor as shown in Table 1. The raw materials were directly mixed to form a powder composition. Alternatively, they were mixed and then dissolved in water to form a solution of the composition. The validamycin used in the Examples could be one of validamycin A to H or a mixture of several of them (no difference was actually found on the inhibitory effect of different isomers on the enzymes), but validamycin A was mainly used. The mixture of trehalose ($\alpha$, $\alpha$), isotrehalose ($\beta$, $\beta$) and neotrehalose ($\alpha$, $\beta$) was used as the trehalose.

TABLE 1

Combination ways for composition of the present invention

| | Algae material | Enzyme inhibitor | Ratio of algae material to enzyme inhibitor (parts by weight) |
|---|---|---|---|
| Composition 1 | Trehalose | Validamycin | 5000:1 |
| Composition 2 | Trehalose | Validamycin | 100000:1 |
| Composition 3 | Trehalose | Validamycin | 200000:1 |
| Composition 4 | Trehalose | Hexaconazole | 5000:1 |
| Composition 5 | Trehalose | Trehazolin | 5000:1 |
| Composition 6 | Algal polysaccharide | Validamycin | 5000:1 |
| Composition 7 | Alginic acid | Validamycin | 50000:1 |

Further, the solid composition or the solution of the composition might be made into preparations by conventional methods, which would not be enumerated here.

Experiment Example 2: In Vivo Absorption of Multi-Functional Composition of the Present Invention 1. Animals and Materials Male ICR mice, 8 weeks old, 20±2 g in body weight, were purchased from Beijing HFK Bioscience Co., Ltd.

The composition used in the present experiment example was the solution of Composition 1. In particular, 15 g of trehalose and 3 mg of validamycin were picked and then dissolved in 100 mL of sterile water for medical use to provide the solution of Composition 1 which was kept for future use.

2. Method

After normally fed for 3 days, the mice fasted for 12 h with water sufficiently supplied. Then, they were randomly divided into 4 groups depending on the blood glucose, i.e., a blank control group, an administration group, and negative control group 1 and negative control group 2. The mice in the administration group were intragastrically given the solution of Composition 1 prepared in this experimental example at a dose of 13.3 mL/kg body weight while the mice in the blank control group were intragastrically given sterile water for medical use at a dose of 13.3 mL/kg body weight. In addition, the mice in negative control group 1 and 2 were respectively intragastrically given the solution of trehalose (0.15 g/mL) and the solution of validamycin (0.3 mg/mL) at the same dose of 13.3 mL/kg body weight. The blood glucose levels before administration and 10 min, 25 min, 40 min and 60 min post administration were measured respectively, and the results were shown in Table 2.

TABLE 2

| | Blood glucose level before administration (mmol/L) | Blood glucose level after administration (mmol/L) | | | |
|---|---|---|---|---|---|
| | | 10 min | 25 min | 40 min | 60 min |
| Blank control group | 4.7 ± 0.35 | 4.8 ± 0.82 | 5.0 ± 0.96 | 5.6 ± 1.42 | 5.1 ± 1.12 |
| Negative control group 1 | 4.9 ± 0.53 | 6.4 ± 0.40 | 9.5 ± 1.00 | 11.0 ± 0.30 | 9.5 ± 1.12 |
| Negative control group 2 | 5.2 ± 0.44 | 5.3 ± 0.45 | 5.7 ± 0.56 | 5.2 ± 0.23 | 5.3 ± 0.20 |
| Administration group | 4.9 ± 0.00 | 5.0 ± 0.49 | 5.1 ± 0.35 | 5.3 ± 0.49 | 5.5 ± 0.99 |

Changes of blood glucose in mice (mmol/L)

The data in Table 2 indicated that no significant difference of blood glucose level was found among the blank control group, negative control group 2 and the administration group, whether before or after administration, whereas the blood glucose level in negative control group 1 increased significantly compared to the blank control group and then dropped to some extent in the later stage post administration. This was because trehalose was a kind of disaccharide. When used alone, it would be decomposed into glucoses by the enzyme in the stomach and intestine which were subsequently absorbed into the blood, resulting in an increased blood glucose level. For this reason, the blood glucose level in negative control group 1 was obviously higher than those in other groups. In the later stage after administration, due to the in vivo glycometabolism, the blood glucose level declined to some extent. On the other hand, when trehalose and validamycin (the enzyme inhibitor) were used together (in the administration group), or the enzyme inhibitor was used alone (negative control group 2), the blood glucose level didn't rise obviously. This on one hand indicated that the enzyme inhibitor wouldn't affect the level of blood glucose. On the other hand, it indicated that trehalose would not be converted into glucoses in vivo which would increase the blood glucose level after absorbed into blood. Rather, the trehalose entered the gastrointestinal tract itself because the enzyme inhibitor prevented trehalose from being decomposed by the enzymes.

Example 3: Application of Multi-Functional Composition of the Present Invention

The composition solutions used in this Example were provided as follows.

Solution of Composition 1: 15 g of trehalose and 3 mg of validamycin were weighed and then dissolved in 100 mL of sterile water for medical use so as to prepare the solution of Composition 1 which was kept for future use.

Solution of Composition 2: 300 g of trehalose and 3 mg of validamycin were weighed and dissolved in 100 mL of sterile water for medical use so as to prepare the solution of Composition 2 which was kept for future use.

Solution of Composition 3: 600 g of trehalose and 3 mg of validamycin were weighed and dissolved in 100 mL of sterile water for medical use so as to prepared the solution of Composition 3 which was kept for future use.

Solution of Composition 4: 15 g of trehalose and 3 mg of hexaconazole were weighted and dissolved in 100 mL of sterile water for medical use so as to prepare the solution of Composition 4 which was kept for future use.

Solution of Composition 5: 15 g of trehalose and 3 mg of trehazolin were weighed and dissolved in 100 mL of sterile water for medical so as use to prepare the solution of Composition 5 which was kept for future use.

Solution of Composition 6: 15 g of algal polysaccharide and 3 mg of validamycin were weighed and dissolved in 100 mL of sterile water for medical use so as to prepare the solution of Composition 6 which was kept for future use.

Solution of Composition 7: 150 g of alginic acid and 3 mg of validamycin were weighed and dissolved in 100 mL of sterile water for medical use so as to prepare the solution of Composition 7 which was kept for future use.

I. Use of Multi-Functional Composition of the Present Invention in Preparation of a Sugar Substitute Product for Diabetics Serving to Lower Blood Glucose (I). Effect of Composition on Reduction of Blood Glucose in Diabetic Mice 1. Animals and Materials Male ICR mice, 8 weeks old, 20±2 g in body weight, were purchased from Beijing HFK Bioscience Co., Ltd.

Also, the solutions of Compositions 1-7 were used in this Example.

2. Methods

I. Modeling: Before experiment started, a 0.1 mol/L sodium citrate buffer (pH4.5) was prepared. It was sterilized in an autoclave and then stored in a refrigerator at 4° C. Before the modeling began, this sodium citrate buffer was used to freshly prepare a 10 mg/mL solution of streptozotocin (STZ) in an ice bath. The mice were fed normally for 3 days, and then they were intraperitoneally administered with the freshly prepared STZ solution at a dose of 45 mg/kg for 5 consecutive days once a day.

II. Treatment: After the model was successfully established, the mice had not been administered with streptozotocin solution were arranged in a group, i.e., the normal group, and normally fed. The diabetic mice were randomly divided into 11 groups depending on blood glucose level, the groups being a model group, administration groups 1 to 7 and negative control groups 1 to 3. The mice in administration groups 1 to 7 were respectively intragastrically given the solution of Composition 1 to 7 prepared in this Example at a dose of 13.3 mL/kg body weight. The mice in the model group were intragastrically given sterile water for medical use at a dose of 13.3 mL/kg body weight. The mice in negative control groups 1 to 3 were respectively intragastrically administered with the solution of trehalose (0.15 g/mL), the solution of validamycin (0.3 mg/mL) and the solution of algal polysaccharides (0.15 g/mL) at a dose of 13.3 mL/kg body weight. The administration was conducted at 9 am and 9 pm every day, and blood glucose level was checked by Roche blood glucose meter once every other week for 5 weeks. The results were shown in Table 3.1.

TABLE 3.1

Blood glucose changes in model of diabetic mice

| Group | Blood glucose level before administration mmol/L | Blood glucose level at different time points after administration mmol/L | | | | |
|---|---|---|---|---|---|---|
| | | 1 week | 2 weeks | 3 weeks | 4 weeks | 5 weeks |
| Normal group | 6.32 ± 2.10 | 6.11 ± 1.11 | 6.12 ± 1.23 | 6.23 ± 1.56 | 6.41 ± 1.20 | 6.20 ± 1.87 |
| Model group | 18.41 ± 2.12 | 20.27 ± 2.10 | 22.57 ± 2.41 | 23.35 ± 2.10 | 23.16 ± 2.03 | 24.11 ± 1.02 |
| Negative control group 1 | 18.40 ± 2.07 | 22.15 ± 2.14 | 24.50 ± 2.35 | 25.33 ± 2.15 | 26.47 ± 2.12 | 27.16 ± 1.01 |
| Negative control group 2 | 18.27 ± 2.13 | 20.20 ± 2.11 | 22.51 ± 2.28 | 23.57 ± 2.06 | 23.57 ± 1.07 | 24.01 ± 1.25 |
| Negative control group 3 | 18.52 ± 2.31 | 21.32 ± 2.21 | 23.24 ± 2.34 | 25.87 ± 2.18 | 26.25 ± 1.27 | 27.54 ± 1.57 |
| Administration group 1 | 18.32 ± 1.95 | 17.87 ± 3.21 | 15.25 ± 1.25 | 12.24 ± 2.35 | 11.20 ± 1.56 | 8.95 ± 2.01 |
| Administration group 2 | 18.67 ± 1.39 | 18.21 ± 2.00 | 17.07 ± 2.60 | 15.24 ± 1.03 | 13.11 ± 2.78 | 10.56 ± 2.10 |
| Administration group 3 | 19.34 ± 2.13 | 20.15 ± 2.17 | 21.50 ± 2.81 | 22.33 ± 2.05 | 22.87 ± 2.36 | 23.76 ± 1.09 |
| Administration group 4 | 18.65 ± 2.03 | 18.00 ± 2.05 | 16.87 ± 1.02 | 15.03 ± 1.05 | 12.55 ± 1.01 | 9.54 ± 1.21 |
| Administration group 5 | 19.45 ± 1.89 | 18.90 ± 2.11 | 16.17 ± 1.65 | 14.34 ± 1.33 | 11.05 ± 2.41 | 9.66 ± 3.00 |
| Administration group 6 | 18.76 ± 3.65 | 17.50 ± 1.11 | 15.77 ± 1.61 | 13.34 ± 1.04 | 11.00 ± 2.01 | 9.87 ± 3.27 |
| Administration group 7 | 18.46 ± 1.65 | 17.95 ± 2.10 | 16.32 ± 1.35 | 14.23 ± 1.65 | 11.95 ± 2.01 | 9.84 ± 3.21 |

The data in Table 3.1 showed a significant difference of the blood glucose level between the model group and the normal group, suggesting the model with diabetic mice had been successfully established. The blood glucose levels in negative control groups 1 to 3 were comparable to that in the model group, indicating that the use of a single component alone had no effect on blood glucose reduction. In contrast, the blood glucose levels in administration groups 1 to 2 and administration groups 4 to 7 were significantly lower than that in the model group. That is, Compositions 1 to 2 and Compositions 4 to 7 all can reduce the level of blood glucose in diabetic mice. Administration group 3 provided no difference in blood glucose level with the model group and negative control groups 1 to 3, suggesting that Composition 3 had not played a role in reducing blood glucose. The reason was that the content of the enzyme inhibitor was too low.

The blood glucose levels in mice from administration groups 1 to 2 and administration groups 4 to 7 were lower than that in negative control groups 1 to 3, so Compositions 1 to 2 and Compositions 4 to 7 were indicated to indeed reduce blood glucose level in diabetic mice. That is, Compositions 1 to 2 and Compositions 4 to 7 played a role in reducing blood glucose and worked one week after administration. In other words, these compositions produced an effect on blood glucose reduction one week post administration.

In the result comparison between administration group 1 and administration group 6, it can be easily found that administration group 1 involving trehalose provided a lower level of blood glucose than administration group 6 involving the algal polysaccharide, showing that trehalose had a better effect on blood glucose reduction than the algal polysaccharide although both two substances were marine algae-derived materials. Meanwhile, the comparison between administration group 1 and administration groups 4 to 5 revealed that administration group 2 involving validamycin provided a lower level of blood glucose than administration groups 4 to 5 involving hexaconazole and trehazolin although all the three were enzyme inhibitors. The difference might be due to a better inhibitory effect of validamycin on the enzyme, and accordingly more marine algae-derived materials were absorbed so as to reduce the blood glucose level. In contrast, as for Compositions 4 to 5 respectively containing hexaconazole and trehazolin, part of the trehaloses might be decomposed in the gastrointestinal tract, so the effect on blood glucose level was inferior to that in administration group 1 involving administration of validamycin.

Data comparison among administration groups 1 to 3 indicated that with the increase of pbw (parts by weight) ratio of trehalose to validamycin, the effect in reducing blood glucose was gradually reduced until zero. Such a fact suggested that with the decrease in concentration of the enzyme inhibitor, the ability of the composition to prevent the marine algae-derived material from being decomposed declined gradually so that the effect in reducing blood glucose became worse and worse. When the pbw ratio of trehalose to validamycin reached 200000:1, the composition no longer had the effect in reducing blood glucose, suggesting the percentage by mass occupied by the enzyme inhibitor cannot be lower than 0.001% in the composition of the present invention.

(II). Effect on Blood Glucose Level in Normal People

Six healthy volunteers were fasted overnight and then were measured for fasting blood glucose. Thereafter, they were orally administered with 200 mL of the solution of Composition 1, or 200 mL of the solution of trehalose (0.15 g/mL), or 200 mL of the solution of validamycin (0.3 mg/mL), or 200 mL of distilled water, as stated in Table 3.2. The blood glucose level in every volunteer was tested before administration and 30 min, 60 min and 120 min post administration. The results were shown in Table 3.2.

TABLE 3.2

Blood glucose level in normal people

| Volunteer | Agent to administer | Blood glucose level before administration mmol/L | Blood glucose level after administration mmol/L | | |
|---|---|---|---|---|---|
| | | | 30 min | 60 min | 120 min |
| A1 | Distilled water | 5.3 | 5.5 | 5.4 | 5.4 |
| B1 | Solution of validamycin | 6.0 | 6.3 | 6.2 | 5.9 |
| C1 | Solution of trehalose | 7.0 | 9.3 | 8.4 | 7.1 |
| | Solution of Composition 1 | 6.7 | 6.5 | 5.5 | 6.3 |
| D1 | Solution of validamycin | 5.3 | 6.7 | 6.6 | 5.3 |
| | Solution of Composition 1 | 5.0 | 5.7 | 4.8 | 4.9 |
| E1 | Solution of Composition 1 | 4.9 | 5.2 | 4.8 | 4.3 |
| F1 | Solution of Composition 1 | 5.3 | 5.0 | 4.9 | 4.8 |

The data in Table 3.2 indicated that the administration of distilled water or solution of validamycin had not effect on the blood glucose level while the administration of the solution of trehalose significantly raised blood glucose level. On the other hand, the solution of Composition 1 not only inhibited the increase of blood glucose level but also reduced the blood glucose level to some extent. At 120 min post administration, volunteers who took the solution of Composition 1 had their levels of blood glucose return to the level before administration and some even showed a blood glucose level lower than that before administration. These suggested that Composition 1 was indeed capable of inhibiting the rise of blood glucose level in normal people and also had a mild effect in reducing blood glucose.

(III). Short-Term Experiment for Treatment in Human Diabetics

Six patients with type-II diabetes were fasted overnight and then measured for fasting blood glucose level. Then they were orally administered with 200 mL of the solution of Composition 1, or 200 mL of solution of trehalose (0.15 g/mL), or 200 mL of the solution of validamycin (0.3 mg/mL), or 200 mL of distilled water, as stated in Table 3.3.

The blood glucose level in every patient was tested before administration and 30 min, 60 min and 120 min post administration. The results were shown in Table 3.3.

TABLE 3.3

Blood glucose level in patients with type-II diabetes in a short-term experiment

| Volunteer | Agent to administer | Blood glucose level before administration mmol/L | Blood glucose level after administration mmol/L | | |
|---|---|---|---|---|---|
| | | | 30 min | 60 min | 120 min |
| A2 | Distilled water | 13.1 | 13.9 | 13.4 | 13.7 |
| B2 | Solution of validamycin | 9.3 | 9.5 | 9.6 | 9.1 |
| C2 | Solution of trehalose | 15.3 | 25.5 | 20.1 | 17.3 |
| | Solution of Composition 1 | 16.9 | 14.8 | 14.3 | 13.9 |
| D2 | Solution of validamycin | 15.5 | 15.7 | 16.1 | 14.8 |
| | Solution of Composition 1 | 15.2 | 13.7 | 13.2 | 12.9 |
| E2 | Solution of Composition 1 | 14.7 | 14.3 | 13.4 | 12.9 |
| F2 | Solution of Composition 1 | 15.2 | 14.1 | 12.7 | 12.3 |

The data in Table 3.3 indicated that the administration of distilled water and of validamycin solution had no influence on blood glucose level in patients with type-II diabetes while the administration of the solution of trehalose significantly raised the blood glucose level. On the other hand, the solution of Composition 1 not only inhibited the increase of blood glucose level but also reduced the blood glucose level to some extent. At 120 min post administration, patients with type-II diabetes who took the solution of Composition 1 had their levels of blood glucose return to the level before administration and some even showed a blood glucose level lower than that before administration. These suggested that Composition 1 was indeed capable of inhibiting the rise of blood glucose level in patients with type-II diabetes and also had a mild effect in reducing blood glucose.

(IV). Long-Term Experiment for Treatment in Human Diabetics

Six patients with type-II diabetes were fasted overnight and then measured for fasting blood glucose level. Then they were orally administered with 200 mL of the solution of Composition 1, or 200 mL of solution of trehalose (0.15 g/mL), or 200 mL of the solution of validamycin (0.3 mg/mL), or 200 mL of distilled water, as stated in Table 3.4. The blood glucose level in every patient was tested before administration and one day, one week, two weeks and one month post administration. The results were shown in Table 3.4.

TABLE 3.4

Blood glucose level in type-II diabetics in a long-term experiment

| Volunteer | Agent to administer | Blood glucose level before administration mmol/L | Blood glucose level after administration mmol/L | | | |
|---|---|---|---|---|---|---|
| | | | 1 day | 1 week | 2 weeks | 1 month |
| A3 | Distilled water | 19.8 | 19.2 | 19.7 | 19.2 | 18.7 |
| B3 | Solution of validamycin | 8.8 | 8.7 | 9.0 | 8.7 | 8.9 |
| C3 | Solution of Composition 1 | 16.9 | 14.8 | 11.7 | 9.3 | 6.7 |
| D3 | Solution of Composition 1 | 15.2 | 13.1 | 10.8 | 8.5 | 6.4 |
| E3 | Solution of Composition 1 | 14.7 | 12.3 | 9.3 | 8.1 | 6.3 |
| F3 | Solution of Composition 1 | 15.2 | 13.2 | 10.1 | 7.5 | 6.1 |

The data in Table 3.4 indicated that the administration of distilled water and the solution of validamycin solution had no influence on blood glucose level in patients with type-II diabetes while the administration of the solution of Composition 1 effectively inhibited the rise of blood glucose level. After treated for one month, patients with type-II diabetes who took the solution of Composition 1 had their levels of blood glucose return to the level close to that of normal persons, suggesting that the long-term use of composition 1 indeed ameliorated the situation in type-II diabetics.

II. Use of Multi-Functional Composition of the Present Invention in Preparation of a Product for Efaecation and Gut Purge (I). Effect of Multi-Functional Composition of the Present Invention on Enterocinesia in Normal Mice 1. Animals and Materials Male ICR mice, 8 weeks old and 20±2 g in body weight, were purchased from Beijing HFK Bioscience Co., Ltd.

Solutions of Compositions 1 to 7 were used in the experiment.

A suspension of carbon powder of 0.1 g/mL was also used. In particular, 1 g of carbon powder was added to and then suspended evenly in 10 mL of normal saline.

2. Method

After the mice were fed normally for 3 days, they were given no food but water for 18-24 h. By the body weight, the mice were randomly divided into 11 groups, i.e., a blank control group, administration groups 1 to 7 and negative control groups 1 to 3. The mice in administration groups 1 to 7 were respectively intragastrically administered with the solutions of Compositions 1 to 7 at a dose of 13.3 mL/kg body weight while the mice in the blank control group were intragastrically given sterile water for medical use at a dose of 13.3 mL/kg body weight. The mice in negative control groups 1 to 3 were respectively intragastrically administered with the solution of trehalose (0.15 g/mL), the solution of validamycin (0.3 mg/mL) and the solution of algal polysaccharide (0.15 g/ml) at a dose of 13.3 mL/kg body weight. At 20 to 30 min post administration, all mice were intragastrically given the suspension of carbon powder at a dose of 0.2 mL/10 g body weight. At 15 to 20 min post the administration of the carbon powder suspension, the mice were killed by cervical vertebrae dislocation and then were quickly dissected to separate the small intestines. The movement distance of the carbon powder (the distance measured from the carbon powder at the forefront to the end of the duodenum closer to heart) and the full length of the small intestine were measured. And the results were shown in Table 4.1.

TABLE 4.1

Enterocinesia in model of normal mice

| | Full length of small intestine (cm) | Movement distance of carbon powder (cm) | Movement distance of carbon powder/full length of small intestine |
|---|---|---|---|
| Blank control group | 45.4 ± 3.13 | 31.0 ± 3.09 | 68.4 ± 6.87% |
| Negative control group 1 | 46.8 ± 2.50 | 33.6 ± 3.40 | 71.9 ± 8.20% |
| Negative control group 2 | 44.2 ± 2.42 | 29.3 ± 2.34 | 66.3 ± 6.57% |
| Negative control group 3 | 43.8 ± 1.46 | 29.6 ± 2.53 | 67.5 ± 8.21% |
| Administration group 1 | 40.3 ± 4.70 | 34.3 ± 5.20 | 85.1 ± 10.10% |
| Administration group 2 | 43.8 ± 5.71 | 32.6 ± 5.04 | 74.6 ± 7.67% |
| Administration group 3 | 43.9 ± 2.58 | 31.0 ± 2.87 | 70.7 ± 7.97% |
| Administration group 4 | 47.3 ± 4.23 | 38.5 ± 4.35 | 81.5 ± 10.21% |
| Administration group 5 | 44.9 ± 4.21 | 36.0 ± 3.31 | 80.2 ± 9.12% |
| Administration group 6 | 46.2 ± 4.56 | 36.2 ± 2.98 | 78.4 ± 8.54% |
| Administration group 7 | 45.6 ± 5.34 | 34.3 ± 2.78 | 75.2 ± 9.76% |

The data in Table 4.1 indicated that the movement distance of carbon powder in the small intestine (movement distance of carbon powder) in mice from negative control groups 1 to 3 was comparable to that in the blank control group. And the ratio of the movement distance of carbon powder to the full length of small intestine did not show any significant difference between negative control groups 1 to 3 and the blank control group, either. These suggested that the use of a single component from the composition alone produced no effect on relaxing bowels and cleaning intestinal tract. The movement distance of carbon powder in administration groups 1 to 2 and administration groups 4 to 7 was longer than that in the blank control group, and the difference was significant. Moreover, the ratio of the movement distance of carbon powder to the full length of small intestine in these administration groups was also significantly higher than that in the blank control group. That is, Compositions 1 to 2 and Compositions 4 to 7 all can smooth the small intestine to allow carbon powder move longer. The movement distance of carbon powder in administration group 3 was not different from that in the blank control group and negative control groups 1 to 3. Also, there was no obvious difference between this group and the blank control group and negative control groups 1 to 3 in terms of the ratio of the movement distance of carbon powder to the full length of small intestine. All these suggested that Composition 3 couldn't play a role in smoothing the small intestine because the content of enzyme inhibitor was too low.

Basically, the movement distance of carbon powder in the small intestines of mice from administration groups 1 to 2 and administration groups 4 to 7 was longer than that in negative control groups 1 to 3, so did the ratio of the movement distance of carbon powder to the full length of small intestine, suggesting that Compositions 1 to 2 and Compositions 4 to 7 indeed can smooth the small intestine to make carbon powder move longer. In other words, these compositions can play a role in relaxing bowels and cleaning intestinal tract. Further, these compositions took effects at 20 to 30 min after administration, achieving the efficacy of relaxing the bowels and purging the gut. Due to individual differences, the movement distance of carbon powder in the small intestine of mice from administration group 2 was that long as that in negative control group 1, but the ratio of the movement distance of carbon powder to the full length of small intestine in administration group 2 was significantly higher than that in negative control group 1. This would support the conclusion that Compositions 1 to 2 indeed had an effect on relaxing bowels and cleaning intestinal tract.

In the comparison between administration group 1 and administration group 6, it can be easily found that administration group 1 involving trehalose provided a longer movement distance of carbon powder than administration group 6 involving the algal polysaccharide, showing that trehalose had a better effect on relaxing bowels and cleaning intestinal tract than the algal polysaccharide although both two substances were marine algae-derived materials. Meanwhile, the comparison between administration group 1 and administration groups 4 to 5 revealed that administration group 2 involving validamycin provided a longer movement distance of carbon powder than administration groups 4 to 5 involving hexaconazole and trehazolin although all the three were enzyme inhibitors. The difference might be due to a better inhibitory effect of validamycin on the enzyme, and accordingly more marine algae-derived materials entered small intestines so as to relax bowels and clean intestinal tract. In contrast, as for Compositions 4 to 5 respectively containing hexaconazole and trehazolin, part of the trehaloses might be decomposed in the gastrointestinal tract, so the effect on relaxing bowels and cleaning intestinal tract was inferior to that in administration group 1 involving administration of validamycin.

Data comparison among administration groups 1 to 3 indicated that with the increase of pbw (parts by weight) ratio of trehalose to validamycin, the effect in relaxing bowels and cleaning intestinal tract was gradually reduced until zero. Such a fact suggested that with the decrease in concentration of the enzyme inhibitor, the ability of the composition to prevent the marine algae-derived material from being decomposed declined gradually so that the effect in relaxing bowels and cleaning intestinal tract became worse and worse. When the pbw ratio of trehalose to validamycin reached 200000:1, the composition no longer had the effect in relaxing bowels and cleaning intestinal tract, suggesting the percentage by mass occupied by the enzyme inhibitor cannot be lower than 0.001% in the composition of the present invention.

(II). Effect on Defecation Quantity in Normal Mice
1. Animals and Materials

Male ICR mice, 8 weeks old and 20±2 g in body weight, were purchased from Beijing HFK Bioscience Co., Ltd.

Composition solution: The solution of Composition 1 prepared in this Example was used.

2. Method

After the mice were fed normally for 3 days, they were given no food but water for 4 h. By body weight, they were randomly divided into two groups, i.e., a control group and an administration group. The mice from the administration group were intragastrically administered with the solution of Composition 1 prepared in this example at a dose of 13.3 mL/kg body weight while the mice from the control group were intragastrically given sterile water for medical use at a dose of 13.3 mL/kg body weight. At 20 to 30 min post administration, mice were allowed to eat freely. The defecation quantity of the mice in each group (the average defecation quantity of the mice in each group) within 1 to 3 h after administration was recorded, and the results were shown in Table 4.2.

TABLE 4.2

Defecation quantity in model of normal mice

| | | Average number of feces granules | |
|---|---|---|---|
| Recording timing | Time | Control group | Administration group |
| Before administration | 4 h | 5.7 | 5.8 |
| | 3 h | 0.9 | 0.8 |
| | 2 h | 1.7 | 1.8 |
| | 1 h | 0.7 | 0.6 |
| After administration | 1 h | 0.6 | 2.6 |
| | 2 h | 0.7 | 1.9 |
| | 3 h | 1.0 | 0.8 |

The data in Table 4.2 indicated that the mice in the control group and the mice in the administration group had comparable number of feces granules before administration, but the number of feces granules in mice from the administration group became obviously more than that in mice from the control group 1 to 2 h post administration. Particularly, the difference reached the maximum 1 h after administration, i.e., the defecation quantity in the administration group was larger than that in the control group by 4.3 times (2.6 in the administration group versus 0.7 in the control group). Again Composition 1 was proven to promote bowel movement in normal mice and to take effect 1 h post administration. The defecation quantity in the mice from the administration group was less than that in mice from the control group 3 h after administration. This was because most feces in the intestinal tract had been discharged in 1 to 2 h post administration and the remaining feces in the intestinal tract decreased significantly. Accordingly, the defecation quantity come out in the administration group was less than the control group at that time. The observation of feces state revealed that the feces of the mice from the administration group were yellowish. The mice in that group had mild diarrhea and there was loose feces near the anus without serious foul odor. The feces of the mice from the control group were black and had foul odor. All these indicated that Composition 1 may make defecation easier and trehalose can wrap the organic acids in the feces which produced foul odor so that an evident efficacy of removing toxins in the intestinal tract can be achieved.

(III). Effect on Defecation Quantity in Mice with Constipation
1. Animals and Materials Male ICR mice, 8 weeks old and 20±2 g in body weight, were purchased from Beijing HFK Bioscience Co., Ltd.

Composition solution: The solution of Composition 1 prepared in this example was used.

2. Experimental Method

After mice were fed normally for 3 days, they were randomly divided into three groups depending on body weights, i.e., a normal group, a control group and an administration group. The mice in the control group and the administration group were given no water but food for 72 h whereas the mice in the normal group were fed normally. Thereafter, the mice in the administration group were intragastrically administered with the solution of Composition 1 at a dose of 13.3 mL/kg body weight, and the mice in the control group were intragastrically administered with sterile water for medical use at a dose of 13.3 mL/kg body weight. Meanwhile, the mice in the normal group were normally fed. At 20 to 30 min post administration, the mice were allowed to eat and drink freely. The defecation quantity in the mice from each group (the average defecation quantity in mice from each group) within 1 to 2 h post administration was recorded and the results were shown in Table 4.3.

TABLE 4.3

Defecation quantity in model of constive mice

| | | Average number of feces granules | | |
|---|---|---|---|---|
| Recording timing | Time | Normal group | Control group | Administration group |
| Before administration | 4 h | 2.0 | 0.9 | 1.0 |
| | 3 h | 1.8 | 1.0 | 0.7 |
| | 2 h | 1.9 | 0.8 | 0.9 |
| | 1 h | 1.9 | 0.6 | 0.8 |
| After administration | 1 h | 1.7 | 0.8 | 3.2 |
| | 2 h | 1.8 | 1.0 | 1.3 |

The data in Table 4.3 indicated that the mice in the control group and the mice in the administration group had comparable number of feces granules before administration, but the number of feces granules in mice from the administration group became obviously more than that in mice from the control group and the normal group 1 to 2 h post administration. Particularly, the difference reached the maximum 1 h after administration, i.e., the defecation quantity in the administration group was larger than that in the control group and the normal group by 1.88 times and 4 times respectively (3.2 in the administration group versus 1.7 in the control group, and 3.2 in the administration group versus 0.8 in the normal group). Composition 1 was proven to promote bowel movement in mice with constipation and to take effect 1 h post administration. The defecation quantity in the mice from the administration group evidently decreased 2 h after administration. This was because most feces in the intestinal tract had been discharged in 1 h post administration and the total feces remaining in the intestinal tract decreased significantly. Accordingly, the defecation quantity in the administration group decreased significantly at that time. The observation on feces state revealed that the feces of the mice from the normal group was blackish green and had mild foul odor and the feces of the mice from the control group were black and had foul odor. On the other hand, the feces of the mice from the administration group were yellowish. The mice in that group had mild diarrhea and there was loose feces near the anus without serious foul odor. All these indicated that Composition 1 may make defecation easier and trehalose can wrap the organic acids in the feces which produced foul odor so that an evident efficacy of removing toxins in the intestinal tract can be achieved.

(IV). Experiment for Treatment in Human Constipation

1. Mr. Liu, a volunteer of 38 years old with a height of 160 cm and a body weight of 60 kg, had mild constipation but had no history of cardiovascular diseases. He was administered with 200 mL of the solution of Composition 1 prepared in this example after fasting, and began to have meal at 30 min after administration. Half an hour after dining, he had a call of nature and defecated once. The feces were mildly loose. This volunteer didn't feel any obvious abdominal distension and abdominal pain or other discomforts throughout the experiment. The present example indicated that the composition of the present invention played a role in relaxing bowels of human and took effect fast without providing any discomforts such as abdominal distension, abdominal pain and diarrhea.

2. Twenty two volunteers meeting the Rome III criteria for functional constipation were selected, including 5 male volunteers and 17 female volunteers, at the age of 18 to 85 (the average age being 48.57±17.43) with a body weight 40 to 83 kg (61.11±12.15 kg on average), a height of 155 to 180 cm (165.26±7.23 cm on average) and a body mass index (BMI) of 15.63 to 28.13 (22.24±3.35 on average). The administration scheme was provided as follows. In particular, they were orally administered with 200 mL of the solution of Composition 1 prepared in this example with empty stomach every morning and then allowed to have breakfast normally half an hour later. The administration was continued for 7 days.

Experimental Results:

1). The frequency of defecation increased significantly in these volunteers. Before administration of Composition 1, the volunteers defecated once every 2 to 3 days on average. Once the administration of Composition 1 started, the volunteers were observed continuously for 7 days. During these 7 days, each volunteer defecated once a day on average. They were continuously observed for another week since the administration of Composition 1 stopped. The results turned out that each volunteer still defecated once a day on average.

2). The difficulty of the volunteers in defecation was alleviated significantly. It was analyzed with defecation difficulty index (the defecation difficulty index was an important index evaluating the degree of constipation in a patient, including three evaluation parameters, i.e., the feeling of incomplete defecation, difficult defecation and anus obstruction, and a scale of 1 to 5 was adopted in the evaluation, i.e., 1. no symptom, 2. slight symptoms exhibited but were tolerable, 3. symptoms exhibited in a relatively obvious manner without disturbance to daily life, 4. symptoms obviously exhibited with disturbance to daily life, 5. serious symptoms exhibited with influence on daily life and work). Before administration of Composition 1, the average defecation difficulty index in volunteers was ranked to be 2.5 to 3. After administration of Composition 1, the defecation difficulty index dropped to 1 or less for 7 days. The volunteers were observed continuously for another 7 days since the administration of Composition 1 stopped, and the results showed that the defecation difficulty index was maintained at 1 or less.

3). Other benign responses in the volunteers were as follows. During the administration of Composition 1, nearly 70% of the volunteers reported a feeling of easiness throughout the whole body that had not shown for a long time. Nearly 30% of the volunteers reported an improvement of complexion, and nearly 25% of volunteers said that their sleeping was improved. Further, some volunteers reported an improved state of health.

4). Other responses in the volunteers were as follows. The volunteers generally reported that they often had a feeling of controllable discomfort in the early stage of the administration of Composition 1 such as increased bowel sound and increased fart. In a few cases, mild abdominal distension, increased numbers of defecation and loose feces were reported. However, these symptoms were tolerable and ameliorated or remitted after about 2 days without any treatments. In some volunteers having obvious symptoms, these symptoms disappeared immediately after the suspension of the administration of Composition 1.

5). Specific manifestations in part of the volunteers were as follows. Volunteer 1, a female of 73 years old, had constipation for many years. She seldom had a call of nature and defecated once every 3 days on average, occasionally with difficulty in defecation. The feces were stinky. She had poor sleep and often had the problems of difficulty in falling asleep, easy to wake up and wake up early. She slept for 4 h a night on average. From Apr. 28, 2013, she began to take Composition 1. In particular, she took 200 mL before breakfast and 200 mL before night sleep. On the first day of administration, she defecated once without difficulty. From the second day of administration, she felt the sleeping was improved. For example, she fell asleep easily and the sleep lasted for 7 to 8 h a night with an improved sleeping quality. She had a feeling of easiness in the whole body next morning that had not come for a long time. After 10 consecutive days of administration, she reported regular daily defecation and sleeping. She also reported that the whole body was at ease and the state of health was good too.

Volunteer 2, a female of 85 years old, was once diagnosed with Parkinson's disease and had constipation for more than 40 years. She defecated once every 4 to 5 days on average, and the feces were dry. She always did the defecation with much effort with hands helping to dig. She ever took various kinds of laxatives, but the effect turned out to be not good. From August 2013, she began to take Composition 1. In the beginning, she took 200 mL before breakfast, but the effect was not that good. Later the dose was gradually increased to 400 mL which was helpful in defecation. She defecated once every 1 to 2 days and feces were all soft. She took Composition 1 for 3 to 4 consecutive days and then suspended the use for 1 to 2 day, which formed an administration cycle for her. After about 1 month, the dose was reduced to 300 mL per day, 1 to 2 times a week.

This experiment confirmed the effect of Composition 1 in relaxing the bowels. It may increase the frequency of defecation, from 2 to 3 times a week to 6 to 7 times a week which was then maintained. As the time relapsed, if the defecation was kept to be normal, then the dose of Composition 1 was reduced gradually. According to the observations in this example, as long as the dose was appropriate, the effect on relaxing the bowels can be achieved on the first day of administration. After that, the administration was performed for 2 to 3 days and then suspended for 1 to 2 days and then again performed for 2 to 3 days. In this way, the bowel relaxing effect would be better. With the improvement of defecation and gastrointestinal function, after 4 cycles mentioned above, the dose of Composition 1 may be reduced gradually and the interval between two administrations may be gradually prolonged while normal defecation could still be kept. Later on, the administration may be stopped or conducted intermittently in accordance with the need.

III. Use of Multi-Functional Composition of the Present Invention in Preparation of a Sliming Product (I). Effect of the Composition on Defecation Quantity in Normal Mice 1. Animals and Materials Male ICR mice, 8 weeks old and 20±2 g in body weight, were purchased from Beijing HFK Bioscience Co., Ltd.

The solutions of Compositions 1 to 7 prepared in this example were used.

2. Method

After the mice were fed normally for 3 days, they were given no food but water for 4 h. By body weight, they were randomly divided into 11 groups, i.e., a blank control group, administration groups 1 to 7 and negative control groups 1 to 3. The mice in administration groups 1 to 7 were intragastrically administered with the solutions of Compositions 1 to 7 respectively at a dose of 13.3 mL/kg body weight. On the other hand, the mice in the blank control group were intragastrically given sterile water for medical use at a dose of 13.3 mL/kg body weight. Further, the mice in negative control groups 1 to 3 were intragastrically given the solution of trehalose (0.15 g/mL), the solution of validamycin (0.3 mg/mL) and the solution of algal polysaccharides (0.15 g/mL) respectively at a dose of 13.3 mL/kg body weight. At 20 to 30 min post administration, mice were allowed to eat freely and the defecation quantity in the mice from each group before and after administration (average feces quantity of the mice in each group), the percentages of defecation quantities before and after administration based on the total defecation quantities throughout the experiment and the body weight were recorded. The results were shown in Table 5.1.

control groups 1 to 3 decreased significantly compared to that in the blank control group but still no significant difference was found in terms of body weight, suggesting that the use of a single component from the composition alone had no effect on weight reduction. In administration groups 1 to 2 and administration groups 4 to 7, the defecation feces quantity and body weight in the mice before administration were both comparable to those in the blank control group. After administration, the defecation quantity in these groups was obviously more than that in the blank control group and body weight was reduced significantly too. That is, Compositions 1 to 2 and Compositions 4 to 7 were capable of reducing the body weight of mice. Before administration, the defecation quantity and body weight in the mice from administration group 3 had no difference compared to those in the blank control group and negative control groups 1 to 3. After administration, the defecation quantity was obviously less than that in the blank control group, but body weight was still not obviously different from that in the blank control group and negative control groups 1 to 3, suggesting that composition 3 couldn't play a role in reducing body weight because the content of the enzyme inhibitor was too low.

After administration, the defecation quantity in mice from administration groups 1 to 2 and administration groups 4 to 7 was more than that in negative control groups 1 to 3 and body weight was lighter than that in negative control groups 1 to 3, suggesting that Compositions 1 to 2 and Compositions 4 to 7 indeed smoothed the small intestines so as to discharge rubbish from the intestinal tract and reduce the body weight. These compositions took effect within 3 h post administration, achieving the sliming efficacy.

On the bias of the comparison between administration group 1 and administration group 6, it can be easily found that administration group 1 involving trehalose provided a

TABLE 5.1

Defecation and body weight changes in model of normal mice

| Group | Stage | defecation quantity g | Percentage of defecation quantity in each stage based the total defecation quantity % | Body weight g |
|---|---|---|---|---|
| Blank control group | Before administration | 1.20 ± 0.04 | 61.54 | 20.50 |
|  | After administration | 0.75 ± 0.01 | 38.46 | 19.75 |
| Negative control group 1 | Before administration | 1.15 ± 0.03 | 62.16 | 19.80 |
|  | After administration | 0.70 ± 0.01 | 37.84 | 19.10 |
| Negative control group 2 | Before administration | 1.23 ± 0.04 | 64.74 | 20.12 |
|  | After administration | 0.67 ± 0.05 | 35.26 | 19.45 |
| Negative control group 3 | Before administration | 1.32 ± 0.03 | 65.67 | 20.16 |
|  | After administration | 0.69 ± 0.04 | 34.33 | 19.47 |
| Administration group 1 | Before administration | 1.32 ± 0.01 | 51.97 | 19.98 |
|  | After administration | 1.22 ± 0.05 | 48.03 | 18.76 |
| Administration group 2 | Before administration | 1.18 ± 0.07 | 55.92 | 20.02 |
|  | After administration | 0.93 ± 0.01 | 44.08 | 19.09 |
| Administration group 3 | Before administration | 1.18 ± 0.04 | 59.60 | 20.34 |
|  | After administration | 0.80 ± 0.01 | 40.40 | 19.54 |
| Administration group 4 | Before administration | 1.21 ± 0.05 | 53.07 | 20.01 |
|  | After administration | 1.07 ± 0.04 | 46.93 | 18.94 |
| Administration group 5 | Before administration | 1.19 ± 0.03 | 53.60 | 20.11 |
|  | After administration | 1.03 ± 0.05 | 46.40 | 19.08 |
| Administration group 6 | Before administration | 1.23 ± 0.07 | 54.91 | 20.00 |
|  | After administration | 1.01 ± 0.01 | 45.09 | 18.99 |
| Administration group 7 | Before administration | 1.29 ± 0.06 | 55.13 | 19.89 |
|  | After administration | 1.05 ± 0.01 | 44.87 | 18.84 |

The data in Table 5.1 indicated that before administration, the defecation quantity in negative control groups 1 to 3 was comparable to that in the blank control group, and no significant difference was found in terms of body weight. After administration, the defecation quantity in negative higher level of defecation quantity after administration than administration group 6 involving the algal polysaccharide and also administration group 1 involving trehalose provided a lighter body weight after administration than administration group 6 involving the algal polysaccharide, showing that trehalose had a better effect on body sliming than the algal polysaccharide although they were both marine algae-derived materials. Meanwhile, the comparison between administration group 1 and administration groups 4 to 5 revealed that administration group 2 involving validamycin provided a higher level of defecation quantity after administration than administration groups 4 to 5 involving hexaconazole and trehazolin and also administration group 2 involving validamycin provided a lighter body weight after administration than administration groups 4 to 5 involving hexaconazole and trehazolin although all the three substances were enzyme inhibitors. The difference might be due to a better inhibitory effect of validamycin on the enzyme, and accordingly more marine algae-derived materials were absorbed into the small intestine so as to reduce the body weight. In contrast, as for Compositions 4 to 5 respectively containing hexaconazole and trehazolin, part of the trehaloses might be decomposed in the gastrointestinal tract, so the sliming effect was inferior to that in administration group 1 involving validamycin.

Data comparison among administration groups 1 to 3 indicated that with the gradual increase of pbw (parts by weight) ratio of trehalose to validamycin, the effect in reducing weight was gradually reduced to zero, suggesting that with the reduction of the concentration of the enzyme inhibitor, the ability of the composition to prevent the marine algae-derived material from being decomposed declined gradually, thus showing a decreasing sliming effect. When the parts by weight ratio of trehalose to validamycin reached 200000:1, the composition no longer had the sliming effect, suggesting that the mass percentage of the enzyme inhibitor cannot be lower than 0.001% in the composition of the present invention.

(II). Effect on Body Weight in Obese Rats

1. Animals and Materials

Male SD rats, 150 g to 180 g in body weight, were purchased from Shanghai Sippr-BK Lab Animal Co., Ltd.

Composition solution: the solution of Composition 1 prepared in this example was used.

2. Method

After the rats were fed normally for 3 days, they were fed with high-fat feedstuff (80% of basal feed, 10% of lard and 10% of yolk powder) for 30 days. By body weight, they were randomly divided into two groups, i.e., a control group and an administration group. The rats in the administration group were intragastrically administered with the solution of Composition 1 at a dose of 13.3 mL/kg body weight while the rats in the control group were intragastrically given sterile water for medical use at a dose of 13.3 mL/kg body weight. The administration was conducted once a day and lasted for 30 days. During the administration period, the rats in the control group and the administration group were still fed with high-fat feedstuff and the body weight was recorded once every week. The results were shown in Table 5.2. Further, the rats fed with basal feed were arranged in a normal group.

TABLE 5.2

Body weight changes in model of obese rats

| Group | Body weight of rats before administration (g) | Body weight of rats after administration (g) | | | |
|---|---|---|---|---|---|
| | | Week 1 | Week 2 | Week 3 | Week 4 |
| Normal group | 189.4 ± 19.3 | 211.2 ± 21.7 | 229.9 ± 22.0 | 252.2 ± 23.8 | 280.9 ± 26.5 |
| Control group | 234.4 ± 20.0 | 267.9 ± 23.2 | 310.1 ± 21.1 | 345.8 ± 27.9 | 352.0 ± 28.5 |
| Administration group | 235.9 ± 19.8 | 260.4 ± 27.7 | 282.7 ± 22.4 | 300.8 ± 21.8 | 310.0 ± 27.3 |

The data in Table 5.2 indicated that in the normal group, the body weight of rats tended to stably increase from about 189 g before administration to about 280 g in the fourth week post administration as the feeding proceeded. Meanwhile, in the control group and the administration group, due to the adoption of high-fat diet, the body weight reached about 235 g before administration which showed a significant difference from the normal group, suggesting the successful establishment of the obese rat model. Before administration, the body weight of the rats in the control group was equivalent to that in the administration group with no significant difference. However, the body weight of the rats in the administration group was obviously lower than that in the control group 1 to 5 weeks post administration. Particularly, at the third week after administration, such a difference reached the maximum and the body weight was reduced by 13% (300.8 of the administration group versus 345.8 of the control group). Again, Composition 1 was proven to significantly reduce the body weight in obese rats and take effect within 1 week. Therefore, Composition 1 was capable of reducing body weight and had an obvious sliming effect.

(III). Experiment in Human Diet

One hundred and seven volunteers with the intention of weight loss were gathered from April 2013 to September 2013, including 39 males with 6 withdrawn from the experiment and 68 femals with 11 withdrawn from the experiment. Among them, 90 volunteers in total received the follow-up. By the time of summarization of this document, 68 volunteers received more than one week's follow-up. The data from these 68 people were analyzed. They had an age of 14 to 78 (41.46±13.27 on average) with a body weight of 49.5 to 130 kg (76.15±15.30 kg on average), a height of 153 to 192 cm (165.48±7.37 cm on average) and a body mass index of 19.83 to 42.45 (27.73±4.50 on average). The administration scheme was provided as follows. In particular, 200 mL of the solution of Composition 1 prepared in this example was given to the empty stomach every morning and then allowed to have breakfast normally half an hour later. The administration lasted for 10 weeks. With respect to the basic diseases, the volunteers were complicated with fatty liver, hypertension, hyperlipidemia, diabetes, constipation, poor sleep and the like.

The change of the average body weight in volunteers was shown in FIG. 1. It can be seen from FIG. 1 that compared with the original average weight, the body weight of these 68 volunteers was reduced by 5 kg after 10 weeks' sliming test, suggesting that Composition 1 did have an obvious sliming effect.

Other experimental results were provided as follows.

1). The frequency of defecation increased significantly in these volunteers. Before administration of Composition 1, the volunteers defecated once every 2 to 3 days on average. Once the administration of Composition 1 started, the volunteers were observed continuously for 7 days. During these 7 days, each volunteer defecated once per day on average. They were continuously observed for another week since the administration of Composition 1 stopped. The results turned out that the costive volunteers still defecated once a day on average.

2). The difficulty of the costive volunteers in defecation was alleviated significantly. It was analyzed with defecation difficulty index (the defecation difficulty index was an important index evaluating the degree of constipation in a patient, including three evaluation parameters, i.e., the feeling of incomplete defecation, difficult defecation and anus obstruction, and a scale of 1 to 5 was adopted in the evaluation, i.e., 1. no symptom, 2. slight symptoms exhibited but were tolerable, 3. symptoms exhibited in a relatively obvious manner without disturbance to daily life, 4. symptoms obviously exhibited with disturbance to daily life, 5. serious symptoms exhibited with influence on daily life and work). Before administration of Composition 1, the average defecation difficulty index in costive volunteers was ranked to be 2.5 to 3. After administration of Composition 1, the defecation difficulty index dropped to 1 or less for 7 days. The volunteers were observed continuously for another 7 days since the administration of Composition 1 stopped, and the results showed that the defecation difficulty index was maintained at 1 or less.

3). Other benign responses in the volunteers were as follows. During the administration of Composition 1, nearly 70% of the volunteers reported a feeling of easiness throughout the whole body that had not shown for a long time. Nearly 30% of the volunteers reported an improvement of complexion, and nearly 25% of volunteers said that their sleeping was improved. Further, some volunteers reported an improved state of health.

4). Other responses in the volunteers were as follows. The volunteers generally reported that they often had a feeling of controllable discomfort in the early stage of the administration of Composition 1 such as increased bowel sound and increased fart. In a few cases, mild abdominal distension, increased numbers of defecation and loose feces were reported. However, these symptoms were tolerable and ameliorated or remitted after about 2 days without any treatments. In some volunteers having obvious symptoms, these symptoms disappeared immediately after the suspension of the administration of Composition 1.

5). Specific manifestations in part of the volunteers were as follows. Volunteer 1, a female of 73 years old, had poor sleep and often had the problems of difficulty in falling asleep, easy to wake up and wake up early. She slept for 4 h a night on average. From Apr. 28, 2013, she began to take Composition 1. In particular, she took 200 mL before breakfast and 200 mL before night sleep. From the second day of administration, she felt the sleeping was improved. For example, she fell asleep easily and the sleep lasted for 7 to 8 h a night with an improved sleeping quality. She had a feeling of easiness in the whole body next morning that had not come for a long time. After 10 consecutive days of administration, she reported regular daily defecation and sleeping. She also reported that the whole body was at ease and the state of health was good too.

The experimental results confirmed the effect of Composition 1 on weight reduction. The body weight was reduced by 5 kg per 10 weeks on average. After the administration was stopped, the body weight was able to maintain at this level and won't bounce back. As the administration continued, if the body weight was kept on losing, the amount of Composition 1 was reduced gradually. According to the experimental observation, as long as the dose was appropriate, the effect of weight reduction can be achieved on the second day of administration.

IV. Use of Multi-Functional Composition of the Present Invention in Preparation of a Beauty Product (I). Determination of Moisture Content in Human Skin 1. Subjects and Materials One hundred and ten people were selected from the volunteers who participating in this test. They were females at the age of 30 to 55 with skin moisture content below 12%.

Solutions of Composition 1 to 7 prepared in this example were used except that the sterile water for medical use was replaced with warm water.

2. Method

By skin moisture content, the subjects were randomly divided into 11 groups, i.e., a blank control group, administration groups 1 to 7 and negative control groups 1 to 3. The subjects in administration groups 1 to 7 respectively took 200 mL of the solution of Compositions 1 to 7 twice a day at 9 am and 9 pm while the subjects in the blank control group took 200 mL of warm water at the same time. In addition, the subjects in negative control groups 1 to 3 respectively took 200 mL of the solution of trehalose (0.15 g/mL), 200 mL of the solution of validamycin (0.3 mg/mL) and 200 mL of the solution of algal polysaccharides (0.15 g/mL). The administration lasted for 30 days. Skin moisture content was determined before administration and after administration. The determination was conducted in a spacious and well ventilated examination room. When the subjects were calm, the location to be determined was cleaned with sterile cotton ball soaked with distilled water. Fifteen minutes after the location was wiped dry, the skin moisture content was determined by skin moisture tester under the trademark of "KAKUSAN". The results were shown in Table 6.1.

TABLE 6.1

Moisture content in human skin

| | Skin moisture content (%) | |
|---|---|---|
| Group | Before administration | After administration |
| Blank control group | 8.32 ± 1.01 | 8.40 ± 0.98 |
| Negative control group 1 | 8.55 ± 0.68 | 8.52 ± 0.55 |
| Negative control group 2 | 8.21 ± 0.98 | 8.35 ± 0.47 |
| Negative control group 3 | 8.35 ± 0.87 | 8.44 ± 0.69 |
| Administration group 1 | 8.39 ± 1.00 | 10.01 ± 0.48 |
| Administration group 2 | 8.47 ± 0.65 | 8.78 ± 0.36 |
| Administration group 3 | 8.34 ± 0.34 | 8.22 ± 0.85 |
| Administration group 4 | 8.33 ± 0.56 | 9.44 ± 0.46 |
| Administration group 5 | 8.65 ± 0.55 | 9.37 ± 0.64 |
| Administration group 6 | 8.41 ± 0.47 | 9.32 ± 0.74 |
| Administration group 7 | 8.11 ± 0.97 | 9.15 ± 0.63 |

The data in Table 6.1 indicated that the skin moisture content in the subjects from negative control groups 1 to 3 was equivalent to that in the blank control group, suggesting that the use of a single component from the composition alone had no effect of increasing the moisture content in skin. The skin moisture content of administration groups 1 to 2 and administration groups 4 to 7 was higher than that of the blank control group, and the difference was significant. That is, Compositions 1 to 2 and Compositions 4 to 7 can all raise the moisture content in skin and also play an effect of maintaining beauty and keeping young. The skin moisture content in administration group 3 was not different from that in the blank control group and negative control groups 1 to 3, indicating that Composition 3 had no effect on raising the moisture content in skin because the content of the enzyme inhibitor was too low.

The subjects in administration groups 1 to 2 and administration groups 4 to 7 all had higher skin moisture content than those in negative control groups 1 to 3, indicating that Compositions 1 to 2 and Compositions 4 to 7 were indeed capable of increasing the moisture content in skin, maintaining beauty and keeping young. The effect became evident just 1 month post administration. In the comparison between administration group 1 and administration group 6, it can be easily found that administration group 1 involving trehalose provided a higher moisture content in skin than administration group 6 involving the algal polysaccharide, showing that trehalose had a better effect on the increase of skin moisture content than the algal polysaccharide although both substances were marine algae-derived materials. Meanwhile, the comparison between administration group 1 and administration groups 4 to 5 revealed that administration group 2 involving validamycin provided a higher moisture content in skin than administration groups 4 to 5 involving hexaconazole and trehazolin although all the three were enzyme inhibitors. The difference might be due to a better inhibitory effect of validamycin on the enzyme, and accordingly more marine algae-derived materials were absorbed into the small intestine so as to increase the moisture content in skin. In contrast, as for Compositions 4 to 5 respectively containing hexaconazole and trehazolin, part of the trehaloses might be decomposed in the gastrointestinal tract, so the effect was inferior to that in administration group 1 involving administration of validamycin.

Data comparison among administration groups 1 to 3 indicated that with the increase of pbw (parts by weight) ratio of trehalose to validamycin, the effect in increasing the moisture content in skin and maintaining beauty was gradually reduced until zero. Such a fact suggested that with the decrease in concentration of the enzyme inhibitor, the ability of the composition to prevent the marine algae-derived material from being decomposed declined gradually so that the effect in maintaining beauty became worse and worse. When the pbw ratio of trehalose to validamycin reached 200000:1, the composition no longer had the effect in increasing the moisture content in skin, suggesting the percentage by mass occupied by the enzyme inhibitor cannot be lower than 0.001% in the composition of the present invention.

(II). Human Experiment on Maintaining Beauty and Keeping Young

1. Volunteer A, a female of 25 years old with a height of 158 cm and a weight of 50 kg, had a quite large area of acne distributed in her face and didn't have a history of the disease. She was not pregnant. She took 200 mL of the solution of Composition 1 prepared in this example with an empty stomach every morning for 30 days. During the experiment, she stopped using other oral or external anti-acne products but had a normal diet without any change in dietary habit. After the experiment was completed, the determined oil content was in the normal range, and the number of acnes was reduced by about 50%. Further, the degree of skin damage was alleviated obviously and became level 1 (on the basis of skin nature and severity of acnes, the acne was clinically classified into 4 levels. level 1: acnes only; level 2: in addition to acnes, there were also a few inflammatory papules; level 3: in addition to acnes, there were also many inflammatory papules or pustules; level 4: in addition to acnes, inflammatory papules and pustules, there were also nodules and cysts). During the administration, the subject didn't have any other discomforts.

2. Volunteer B, a female of 35 years old with a height of 160 cm and a weight of 55 kg, had a number of chloasmas in her face and didn't have a history of the disease. She was not pregnant. She took 200 mL of the solution of Composition 1 prepared in this example with an empty stomach every morning for 30 days. During the experiment, she stopped using other oral or external anti-chloasma products but had a normal diet without any change in dietary habit. When the experiment was completed, the area with chloasma in the face decreased and the color became lighter. During the administration, the subject didn't have any other discomforts.

3. Volunteer C, a female of 20 years old with a height of 163 cm and a weight of 62 kg, had rough skin with a touch of grit. She took 200 mL of the solution of Composition 1 prepared in this example twice a day, before breakfast and before the night sleep. After one month of administration, her state of health was improved obviously with the skin being smooth and delicate, and she did not have any discomfort.

The experimental results had proven the effect of Composition 1 on maintaining beauty and keeping young. This was because trehalose had an excellent non-specific protection to biological cells and may improve the resistance of biological cells to harsh conditions such as a high temperature, dryness and coldness. As the administration of Composition 1 continued, if the skin would maintain normal, the dose of Composition 1 may reduce gradually. Later on, the administration may be stopped or took intermittently according to the need.

V. Use of Multi-Functional Composition of the Present Invention in Preparation of a Product for Improving Sleep (I). Effect of Composition on Sleep in Normal Mice 1. Animals and Materials Male ICR mice, 8 weeks old and 20±2 g in body weight, were purchased from Beijing HFK Bioscience Co., Ltd.

The solutions of Compositions 1 to 7 prepared in this example were used.

2. Method

After the mice were fed normally for 3 days, they were given no food but water for 18 to 24 h. By body weight, the mice were randomly divided into 11 groups, i.e., a blank control group, administration groups 1 to 7 and negative control groups 1 to 3. The mice in administration groups 1 to 7 were intragastrically administered with the solutions of Compositions 1 to 7 at a dose of 13.3 mL/kg body weight while the mice in the blank control group were intragastrically given sterile water for medical use at a dose of 13.3 mL/kg body weight. The mice in negative control groups 1 to 3 were intragastrically given the solution of trehalose (0.15 g/mL), the solution of validamycin (0.3 mg/mL) and the solution of algal polysaccharides (0.15 g/mL) at a dose of 13.3 mL/kg body weight respectively. Twenty to 30 min post administration, all mice were intraperitoneally injected with sodium pentobarbital at a subdissociative dose (15 mg/kg). The time when the righting reflex disappeared and sleep duration of the mice were recorded. The results were shown in Table 7.1.

TABLE 7.1

Time when righting reflex disappeared and
sleep duration in model of normal mice

| Group | Time when righting reflex disappeared (min) | Sleep duration (min) |
| --- | --- | --- |
| Blank control group | 2.51 ± 0.20 | 31.00 ± 3.91 |
| Negative control group 1 | 2.49 ± 0.14 | 30.54 ± 2.17 |
| Negative control group 2 | 3.11 ± 0.21 | 29.87 ± 1.58 |
| Negative control group 3 | 3.24 ± 0.08 | 29.17 ± 2.01 |
| Administration group 1 | 2.02 ± 0.31 | 42.63 ± 5.40 |
| Administration group 2 | 2.35 ± 0.08 | 37.65 ± 1.99 |
| Administration group 3 | 3.01 ± 0.09 | 30.14 ± 2.19 |
| Administration group 4 | 2.05 ± 0.04 | 41.54 ± 2.54 |
| Administration group 5 | 1.99 ± 0.01 | 40.98 ± 3.39 |
| Administration group 6 | 2.09 ± 0.11 | 41.01 ± 4.41 |
| Administration group 7 | 1.98 ± 0.2 | 40.27 ± 1.68 |

The data in Table 7.1 indicated that the time when righting reflex disappeared in mice from negative control groups 1 to 3 was equivalent to that in the blank control group and no difference was found in terms of the sleep duration, suggesting that the use of a single component from the composition alone had no effect on sleeping improvement. In administration groups 1 to 2 and administration groups 4 to 7, the righting reflex disappeared earlier than that in the blank control group, and the difference was significant. Also, the sleep duration in these administration groups was longer than that in the blank control group, suggesting that Compositions 1 to 2 and Compositions 4 to 7 were capable of improving the sleep quality in mice. The time when righting reflex disappeared in mice from administration group 3 was not different from that in the blank control group or negative control groups 1 to 3, neither was the sleep duration. This suggested that Composition 3 couldn't play a role in improving sleep because the content of the enzyme inhibitor was too low.

The righting reflex in administration groups 1 to 2 and administration groups 4 to 7 all disappeared later than that in negative control groups 1 to 3, and the sleep duration in these administration groups were longther than that in negative control groups 1 to 3, indicating that Compositions 1 to 2 and Compositions 4 to 7 were indeed capable of making mice fall asleep more quickly and also prolonging their sleep duration so that the sleep quanlity in mice was improved. Moreover these compositions took effect 20 to 30 min after administration, achieving the efficacy of improving sleep.

In the comparison between administration group 1 and administration group 6, it can be easily found that administration group 1 involving trehalose had the righting reflex disappear earlier than administration group 6 involving the algal polysaccharide, showing that trehalose had a better effect on sleeping improvement than the algal polysaccharide although both substances were marine algae-derived materials. Meanwhile, the comparison between administration group 1 and administration groups 4 to 5 revealed that administration group 2 involving validamycin had the righting reflex disappear earlier than administration groups 4 to 5 involving hexaconazole and trehazolin although all the three were enzyme inhibitors. The difference might be due to a better inhibitory effect of validamycin on the enzyme, and accordingly more marine algae-derived materials were absorbed into the small intestine so as to improve the sleeping. In contrast, as for Compositions 4 to 5 respectively containing hexaconazole and trehazolin, part of the trehaloses might be decomposed in the gastrointestinal tract, so the effect on sleeping improvement was inferior to that in administration group 1 involving administration of validamycin.

Data comparison among administration groups 1 to 3 indicated that with the increase of pbw (parts by weight) ratio of trehalose to validamycin, the effect on sleeping improvement was gradually reduced until zero. Such a fact suggested that with the decrease in concentration of the enzyme inhibitor, the ability of the composition to prevent the marine algae-derived material from being decomposed declined gradually so that the effect on sleeping improvement became worse and worse. When the pbw ratio of trehalose to validamycin reached 200000:1, the composition no longer had the effect on sleeping improvement, suggesting the percentage by mass occupied by the enzyme inhibitor cannot be lower than 0.001% in the composition of the present invention.

(II). Human Experiment on Improvement of Sleep Quality

1. Ten volunteers who meet the diagnosis standard for persistent insomnia and had the intention to improve sleeping were selected, including 5 males and 5 females, at the age of 31 to 61. The specific administration scheme was provided as follows. In particular, 200 mL of the solution of Composition 1 prepared in this example was orally administered every night before sleep for 7 days with the administration of other sleep-producing drugs all stopped.

Experimental results were provided as follows.

(1). Eight out of the 10 volunteers gradually had sleep improvement after regular administration of the composition of the present invention for about one week, as characterized by: 1) easy to fall asleep, 2) hardly waking up during natural sleep, 3) easy to fall asleep again, 4) a cool mind after getting up in the morning.

(2). Other benign responses in volunteers were as follows. During administration of Composition 1, nearly 70% of the volunteers reported a feeling of easiness throughout the whole body that had not shown for a long time. Nearly 30% of the volunteers reported an improvement of complexion, and nearly 25% of volunteers said that their symptoms of migraine and neurasthenia were alleviated significantly and some volunteers reported an improved state of health.

2. Volunteer Mr. Liu, 58 years old, appeared with mild impaired glucose tolerance and didn't have a history of cardiovascular disease. He suffered from insomnia and bad sleeping for a long time, woke up early and felt tired after waking up. He took 200 mL of the solution of Composition 1 prepared in this example half an hour before sleep every night for two weeks. The time he struggled to fall asleep was shortened obviously, and the sleep time became longer. Further, he seldom had dreams during sleep and felt energetic after getting up in the early morning. During administration, the subject didn't have any other discomforts.

Volunteer Ms. Zhao, 40 years old, suffered from moderate persistent insomnia. She took 200 mL of the solution of Composition 1 prepared in this example half an hour before sleep every night. No effect was found until one week later. Although she was busy with work and went to sleep at about 2 to 3 am every day during the administration period, she fell asleep faster than before and the sleep quality was good. Moreover, she felt energetic without the feeling of dizziness and fatigue after she got up in the morning.

The experimental results had proven the effect of Composition 1 on sleep improvement. In particular, it can shorten the time spent in falling asleep and also improve the sleep quality. As the administration of Composition 1 continued, if normal sleep can be ensured, the dose of Composition 1 can be gradually reduced. According to the experimental observation, as long as the dose was appropriate, the effect on sleep improvement can be found on the first day of administration. When the sleep became regular, the administration was conducted for 2 to 3 days and then suspended for 1 to 2 days followed by another 2 to 3 days of administration. In this way, the effect would be rather good. With the gradual improvement of sleep quality, after 4 cycles of the process mentioned above, the dose of Composition 1 may be reduced gradually and the interval between two administrations may be gradually prolonged too while normal sleep was assured. Later on, the administration may be stopped or conducted intermittently according to the need.

VI. Use of Multi-Functional Composition of the Present Invention in Preparation of a Product for Ameliorating Osteoporosis (1). Effect of Composition on Osteoporosis Amelioration in Ovariectomized Rats 1. Animals and Materials Female SD rats, 250 g to 280 g in body weight, were purchased from Shanghai Sippr-BK Lab Animal Co., Ltd.

The solutions of Compositions 1 to 7 prepared in this example were used.

2. Method

After receiving ovariectomy, rats were fed normally for one week. By body weight, the rats were randomly divided into 11 groups, i.e., a blank control group, administration groups 1 to 7 and negative control groups 1 to 3. The rats in administration groups 1 to 7 were intragastrically administered with the solutions of Compositions 1 to 7 respectively at a dose of 13.3 mL/kg body weight while the rats in the blank control group were intragastrically given sterile water for medical use at a dose of 13.3 mL/kg body weight. The rats in negative control groups 1 to 3 were intragastrically given the solution of trehalose (0.15 g/mL), the solution of validamycin (0.3 mg/mL) and the solution of algal polysaccharides (0.15 g/mL) at a dose of 13.3 mL/kg body weight respectively. Administration was conducted once a day and lasted for 30 days. Normal rats were arranged in a normal group and fed normally all the time. Twenty to 30 min post last administration, all rats were killed by cervical vertebrae dislocation, and their femurs were taken out. Then, the bone density and mineral content in the femur were determined. The results were shown in Table 8.1.

TABLE 8.1

Bone density and mineral content in femur in model of ovariectomized rats

| Group | Bone density (g/cm$^2$) | Mineral content (g/cm) |
| --- | --- | --- |
| Normal group | 0.1572 ± 0.0123 | 0.2045 ± 0.0377 |
| Blank control group | 0.1024 ± 0.0201 | 0.1261 ± 0.0306 |
| Negative control group 1 | 0.1037 ± 0.0211 | 0.1245 ± 0.0374 |
| Negative control group 2 | 0.1063 ± 0.0222 | 0.1212 ± 0.0311 |
| Negative control group 3 | 0.1087 ± 0.0285 | 0.1276 ± 0.0333 |
| Administration group 1 | 0.1450 ± 0.0174 | 0.1885 ± 0.0295 |
| Administration group 2 | 0.1208 ± 0.0611 | 0.1524 ± 0.0775 |
| Administration group 3 | 0.1019 ± 0.0301 | 0.1301 ± 0.0201 |
| Administration group 4 | 0.1428 ± 0.0114 | 0.1709 ± 0.0114 |
| Administration group 5 | 0.1368 ± 0.0501 | 0.1684 ± 0.0112 |
| Administration group 6 | 0.1399 ± 0.0427 | 0.1701 ± 0.0110 |
| Administration group 7 | 0.1291 ± 0.0120 | 0.1698 ± 0.0192 |

The data in Table 8.1 indicated that the bone density of femur (hereinafter referred to as "bone density") and mineral content in femur (hereinafter referred to as "mineral content") in rates from the blank control group were obviously lower than those in the normal group, suggesting that the rat model of osteoporosis was successfully established. On this basis, comparison was made. The bone density and mineral content in negative control groups 1 to 3 were equivalent to those in the blank control group, suggesting that the use of a single component from the composition alone had no effect of increasing bone density and mineral content (i.e., the effect of ameliorating osteoporosis). The bone density and mineral content in rats from administration groups 1 to 2 and administration groups 4 to 7 were higher than those in the blank control group, and the difference was significant. That is, Compositions 1 to 2 and Compositions 4 to 7 all can increase the bone density and mineral content to ameliorate osteoporosis. The bone density and mineral content in administration group 3 were not different from those in the blank control group and negative control groups 1 to 3, suggesting that Composition 3 couldn't play a role in ameliorating osteoporosis because the content of the enzyme inhibitor was too low.

Compared to negative control groups 1 to 3, administration groups 1 to 2 and Administration groups 4 to 7 had higher bone density and mineral content, suggesting Compositions 1 to 2 and Compositions 4 to 7 were indeed capable of increasing the bone density and mineral content so that osteoporosis can be ameliorated.

In the comparison between administration group 1 and administration group 6, it can be easily found that administration group 1 involving trehalose had higher bone density and mineral content than administration group 6 involving the algal polysaccharide, showing that trehalose had a better effect on osteoporosis amelioration than the algal polysaccharide although both substances were marine algae-derived materials. Meanwhile, the comparison between administration group 1 and administration groups 4 to 5 revealed that administration group 2 involving validamycin had higher bone density and mineral content than administration groups 4 to 5 involving hexaconazole and trehazolin although all the three were enzyme inhibitors. The difference might be due to a better inhibitory effect of validamycin on the enzyme, and accordingly more marine algae-derived materials were absorbed into the small intestine so as to ameliorate osteoporosis. In contrast, as for Compositions 4 to 5 respectively containing hexaconazole and trehazolin, part of the trehaloses might be decomposed in the gastrointestinal tract, so the effect on osteoporosis amelioration was inferior to that in administration group 1 involving administration of validamycin.

Data comparison among administration groups 1 to 3 indicated that with the increase of pbw (parts by weight) ratio of trehalose to validamycin, the effect on osteoporosis amelioration was gradually reduced until zero. Such a fact suggested that with the decrease in concentration of the enzyme inhibitor, the ability of the composition to prevent the marine algae-derived material from being decomposed declined gradually so that the effect on osteoporosis amelioration became worse and worse. When the pbw ratio of trehalose to validamycin reached 200000:1, the composition no longer had the effect on osteoporosis amelioration, suggesting the percentage by mass occupied by the enzyme inhibitor cannot be lower than 0.001% in the composition of the present invention.

(II). Effect on Bone Development in Normal Juvenile Rats

1. Animals and Materials

Weaned SD rats, 8 weeks old and 20±2 g in body weight, were purchased from Shanghai Sippr-BK Lab Animal Co., Ltd.

Composition solution: the solution of Composition 1 prepared in this example was used.

2. Method

After the rats were fed normally for 3 days, they were divided into three groups depending on body weight, i.e., a normal group, a control group and an administration group. The rats in the administration group and the control group were intragastrically given the solution of Composition 1 prepared in this example and sterile water for medical use respectively at a dose of 13.3 mL/kg body weight twice a day at 9 am and 9 pm. The administration lasted for 5 weeks. The rats in the normal group were fed normally. Twenty to 30 min post last administration, the rats were anesthetized and killed. The femurs on both sides were taken out. The length, weight, bone density and mineral content of the femur were determined then. The results were shown in Table 8.2.

TABLE 8.2

Bone development in model of normal juvenile rats

| Group | Femur length (cm) | Femur weight (g) | Bone density (g/cm$^2$) | Mineral content (g) |
|---|---|---|---|---|
| Normal group | 3.12 ± 0.09 | 0.604 ± 0.201 | 0.1398 ± 0.1420 | 0.1834 ± 0.0142 |
| Control group | 3.22 ± 0.18 | 0.611 ± 0.123 | 0.1432 ± 0.0186 | 0.1826 ± 0.0367 |
| Administration group | 3.95 ± 0.11 | 0.692 ± 0.108 | 0.1655 ± 0.0114 | 0.1942 ± 0.0223 |

The data in Table 8.2 indicated that the length, weight, bone density and mineral content of femur in the control group were not significantly different from those in the normal group. Compared to the normal group and the control group, the length, weight, bone density and mineral content of femur all significantly increased in the administration group. All these indicated that Composition 1 was capable of promoting bone development in juvenile rats and increasing bone density and mineral content of the femur in juvenile rats. Based on this conclusion, it was indicated that Composition 1 can ameliorate osteoporosis.

(III). Experiment on Osteoporosis Amelioration in Humans

1. Volunteer A, a female of 70 years old, had suffered from osteoporosis for many years. The main symptoms were lumbago and back pain, which would be exacerbated after long sitting or standing. From Jun. 21, 2013, she began to take 200 mL of the solution of Composition 1 prepared in this example before breakfast and then another 200 mL before sleep at night. After 30 days' continuous administration, she felt easiness in the whole body and also reported a good state of health. The lumbago and back pain was obviously alleviated and the outdoor activities were increased.

2. Volunteer B, a female of 65 years old, was diagnosed with osteoporosis many years ago. From Jun. 25, 2013, she began to take 200 mL of the solution of Composition 1 as prepared in this example before breakfast and then another before sleep at night. After about one month's administration, lumbar pain was alleviated obviously, so she did more walking. She was reexamined in the hospital and the result indicated that osteoporosis was ameliorated greatly. In the subsequent administration, the dose of the solution of Composition 1 was reduced to 150 mL every morning and another 150 mL at night, 1 to 2 times a week. The symptoms of osteoporosis were then well controlled.

3. Volunteer C, a female of 61 years old, suffered from senile osteoporosis. The main symptoms were lumbago and back pain, and weakened respiratory function accompanied with oppression in chest or the like. From Aug. 21, 2013, she began to take 200 mL of the solution of Composition 1 as prepared in this example before breakfast and another 200 mL before sleep at night. After half an month, lumbago and back pain was alleviated obviously. Then the administration continued for another month, the respiratory function was recovered, oppression in chest disappeared and the condition of osteoporosis was greatly ameliorated.

The experiment results had proven the effect of Composition 1 on osteoporosis amelioration where the bone density and mineral content can be increased and other discomforts brought by osteoporosis can be alleviated and eliminated. As the administration of Composition 1 continued, if the osteoporosis was being ameliorated, then the dose of Composition 1 can be gradually reduced.

VII. Use of Multi-Functional Composition in the Present Invention in Preparation of a Product for Ameliorating Menstrual Disorder (I). Effect of Composition on Pain in Normal Mice 1. Animals and Materials Male ICR mice, 8 weeks old and 20±2 g in body weight, were purchased from Beijing HFK Bioscience Co., Ltd.

The solutions of Compositions 1 to 7 prepared in this example were used.

2. Method

After mice were normally fed for 3 days, they were randomly divided into 11 groups depending on body weight, i.e., a blank control group, administration groups 1 to 7 and negative control groups 1 to 3, by body weight. The mice in administration groups 1 to 7 were intragastrically given the solutions of Compositions 1 to 7 respectively at a dose of 13.3 mL/kg body weight while the mice in the blank control group were intragastrically given sterile water for medical use at a dose of 13.3 mL/kg body weight. The mice in negative control groups 1 to 3 were intragastrically given the solution of trehalose (0.15 g/mL), the solution of validamycin (0.3 mg/mL) and the solution of algal polysaccharides (0.15 g/mL) at a dose of 13.3 mL/kg body weight respectively. Twenty minutes after the administration, the mice were intraperitoneally administered with 0.2 ml of solution of acetic acid (0.6%). Then, the number of writhing and time when initial writhing occurred in mice were observed within 30 min after injection of acetic acid solution and the pain inhibition ratio (pain inhibition ratio=(number of writhings in the blank control group—number of writhings in the administration group)/number of writhings in the blank control group) was calculated. The results were shown in Table 9.1.

TABLE 9.1

Writhing in model of normal mice

| Group | Time of initial writhing (min) | Number of writhings | Pain inhibition ratio |
|---|---|---|---|
| Blank control group | 3.5 ± 2.3 | 51.0 ± 6.0 | 0.0% |
| Negative control group 1 | 3.4 ± 1.1 | 51.3 ± 1.6 | 0.0% |

TABLE 9.1-continued

Writhing in model of normal mice

| Group | Time of initial writhing (min) | Number of writhings | Pain inhibition ratio |
|---|---|---|---|
| Negative control group 2 | 3.6 ± 1.6 | 51.9 ± 2.1 | 0.0% |
| Negative control group 3 | 3.5 ± 2.0 | 52.1 ± 2.3 | 0.0% |
| Administration group 1 | 5.8 ± 3.1 | 26.0 ± 4.0 | 49.0% |
| Administration group 2 | 4.0 ± 2.4 | 41.1 ± 1.4 | 19.4% |
| Administration group 3 | 3.4 ± 3.2 | 50.2 ± 1.8 | 0.1% |
| Administration group 4 | 5.2 ± 5.1 | 34.9 ± 2.1 | 31.6% |
| Administration group 5 | 4.9 ± 1.1 | 33.9 ± 3.7 | 33.5% |
| Administration group 6 | 5.1 ± 3.9 | 34.5 ± 4.9 | 32.4% |
| Administration group 7 | 5.1 ± 3.1 | 36.9 ± 4.0 | 27.6% |

The data in Table 9.1 indicated that the number of writhings in the mice from negative control groups 1 to 3 was equivalent to that in the blank control group and no difference was found in terms of the time of initial writhing, suggesting that the use of a single component from the composition alone had no effect on pain amelioration. The initial writhing occurred later in mice from administration groups 1 to 2 and administration groups 4 to 7 than that in the blank control group, and the difference was significant. Moreover, the number of writhings in these administration groups was significantly more than that in the blank control group. That is, Compositions 1 to 2 and Compositions 4 to 7 all could alleviate the pain in the mice. The time of initial writhing in administration group 3 was not different from that in the blank control group and negative control groups 1 to 3, so was the number of writhings. This suggested that Composition 3 couldn't play a role in pain amelioration because the content of the enzyme inhibitor was too low.

The initial writhing occurred later in mice from administration groups 1 to 2 and administration groups 4 to 7 than that in negative control groups 1 to 3, and the number of writhings in these administration groups was larger than that in negative control groups 1 to 3, suggesting that Compositions 1 to 2 and Compositions 4 to 7 were indeed capable of alleviating pain caused by acetic acid so as to play a role in stopping pain. They took effect 20 to 30 min after administration, achieving the efficacy of alleviating pain.

In the comparison between administration group 1 and administration group 6, it can be easily found that the initial writhing occurred later in administration group 1 involving trehalose than administration group 6 involving the algal polysaccharide. Also, the number of writhing and the pain inhibition ratio in administration group 1 were respectively lower and higher than those in administration group 6. All these suggested that trehalose had a better effect on pain amelioration than the algal polysaccharide although both substances were marine algae-derived materials. Meanwhile, the comparison between administration group 1 and administration groups 4 to 5 revealed that the initial writhing occurred later in administration group 2 involving validamycin than administration groups 4 to 5 respectively involving hexaconazole and trehazolin. Also, the number of writhing and the pain inhibition ratio in administration group 2 were respectively lower and higher than those in administration groups 4 and 5 although all the three substances were enzyme inhibitors. The differences might be due to a better inhibitory effect of validamycin on the enzyme, and accordingly more marine algae-derived materials were absorbed into the small intestine so as to ameliorate pain. In contrast, as for Compositions 4 to 5 respectively containing hexaconazole and trehazolin, part of the trehaloses might be decomposed in the gastrointestinal tract, so the effect on pain amelioration was inferior to that in administration group 1 involving administration of validamycin.

Data comparison among administration groups 1 to 3 indicated that with the increase of pbw (parts by weight) ratio of trehalose to validamycin, the effect on pain amelioration was gradually reduced until zero. Such a fact suggested that with the decrease in concentration of the enzyme inhibitor, the ability of the composition to prevent the marine algae-derived material from being decomposed declined gradually so that the effect on pain amelioration became worse and worse. When the pbw ratio of trehalose to validamycin reached 200000:1, the composition no longer had the effect on pain amelioration, suggesting the percentage by mass occupied by the enzyme inhibitor cannot be lower than 0.001% in the composition of the present invention.

(II). Effect on Count of Red Blood Cells and Hemoglobin Concentration in Mice with Anemia 1. Animals and Materials Female ICR mice, 8 weeks old and 20±2 g in body weight, were purchased from Beijing HFK Bioscience Co., Ltd.

Composition solution: the solution of Composition 1 prepared in this example was used.

2. Method

After the mice were fed normally for 3 days, they were divided into four groups by body weight, i.e., a normal group, a model group, a control group and an administration group. The mice in the administration group were intragastrically administered with the solution of Composition 1 every morning at a dose of 13.3 mL/kg body weight and also with mitomycin every afternoon at a dose of 1 mL/kg body weight. The mice in the control group were intragastrically administered with sterile water for medical use every morning at a dose of 13.3 mL/kg body weight and also with mitomycin every afternoon at a dose of 1 mL/kg body weight. Further, the mice in the model group were intragastrically given mitomycin every afternoon at a dose of 1 mL/kg body weight while the mice in the normal group were normally raised. The administration lasted for 5 days. After the last administration, blood samples were collected and the count of red blood cells and the concentration of hemoglobin in mice from each group were determined. The results were shown in Table 9.2.

TABLE 9.2

Count of red blood cells and concentration of hemoglobin in model of mice with anemia

| Group | Count of red blood cells (×10$^{12}$/L) | concentration of hemoglobin (g/L) |
|---|---|---|
| Normal group | 9.78 ± 1.05 | 108.91 ± 3.51 |
| Model group | 4.86 ± 1.72 | 58.62 ± 5.83 |
| Control group | 5.01 ± 0.89 | 60.98 ± 2.01 |
| Administration group | 6.70 ± 1.64 | 85.03 ± 7.66 |

The data in Table 9.2 indicated that the count of red blood cells and concentration of hemoglobin in mice from the model group were evidently different from those from the blank control group, suggesting that the model of mice with anemia was successfully established. The count of red blood cells and the concentration of hemoglobin in the administration group were both greater than those in the control group and the model group and the difference was significant. That is, Composition 1 can promote the generation of red blood cells in mice and also increase the concentration of hemoglobin in the blood so as to treat the iron deficiency anemia to some extent.

(III). Experiment on Amelioration of Menstrual Disorder in Females

1. Volunteer 1, a female of 35 years old with a height of 160 cm and a body weight of 50 kg, was married with a child. The breast distending pain was serious just before menstruation, and the menstrual cycle was in disorder accompanied with dysmenorrhea and the mood was unstable during menstruation. She ever took traditional Chinese medicine to deal with the situation, but the effect was not good. She didn't have a history of cardiovascular disease. She took 200 mL of the solution of Composition 1 twice a day in the morning and evening respectively, for 3 months. In the third week of the administration of Composition 1, menses came with a moderate quantity. Further, no obvious dysmenorrhea was reported except occasional expansion in lower abdomen, and the breast distending pain before menstruation was gone completely. In particular, the state of health was good with the whole body was at ease. Also, the mood was stable during menstruation and there wasn't any other discomfort. After 3 months, the menstrual cycle was maintained at a normal state with 28 days.

2. Volunteer 2, a female of 27 years old with a height of 170 cm and a body weight of 60 kg, was unmarried and had no child. She had a history of chronic diarrhea, and the menstrual cycle was irregular with menses often happening about 3 days later or earlier than the presumed date. The dysmenorrheal occurred every time and the menstruation lasted for about 1 week. From one week before menstruation, she took 200 mL of the solution of Composition 1 twice a day in the morning and evening till the menstruation ended. She took the composition for 3 months in this way. During the administration period, farting was more frequent, but there was no foul odor and she didn't feel other discomforts. In the first month of the administration, the menstruation came 3 days later than the presumed date. After that, the menstrual cycle was normal with 28 days. Since the administration of Composition 1, menstrual discomfort and dysmenorrhea were alleviated obviously.

3. Volunteer 3, a female of 35 years old, was married with no child. In the recent 2 years, she put on weight obviously. Menopause had lasted for one year. She sought medical advice from many places and was told it had a relation with endocrine disorder. The effect of drug therapies was little. She took 200 mL of the solution of Composition 1 before three meals every day, for 3 months. Two months later, menstruation appeared and no discomfort was felt.

The experiment results had proven the effect of Composition 1 in ameliorating menstrual disorder. As the administration of Composition 1 continued, if a normal menstrual cycle was kept, the dose of Composition 1 may be gradually reduced. With the improvement of menstrual cycle, the dose of Composition 1 may be gradually reduced. Also, the administration may be interrupted appropriately and the time of interruption may be gradually lengthened. In this way, a normal menstrual cycle can be assured. Later on, the administration may be stopped or conducted intermittently according to the need.

VIII. Use of Multi-Functional Composition of the Present Invention in Preparation of an Anti-Fatigue Product (I). Effect of Composition on Loaded Swimming in Normal Mice 1. Animals and Materials Female ICR mice, 8 weeks old and 20±2 g in body weight, were purchased from Beijing HFK Bioscience Co., Ltd.

The solutions of Composition 1 to 7 prepared in this example were used.

2. Method

After the mice were fed normally for 3 days, they were randomly divided into 11 groups by body weight, i.e., a blank control group, administration groups 1 to 7 and negative control groups 1 to 3. The mice in administration groups 1 to 7 were intragastrically administered with the solution of Compositions 1 to 7 respectively a dose of 13.3 mL/kg body weight while the mice in the blank control group were intragastrically given sterile water for medical use at a dose of 13.3 mL/kg body weight. The mice in negative control groups 1 to 3 were intragastrically given the solution of trehalose (0.15 g/mL), the solution of validamycin (0.3 mg/mL) and the solution of algal polysaccharides (0.15 g/mL) respectively at a dose of 13.3 mL/kg body weight. Twenty minutes after the administration, a weight of 2 g was fixed to the tail of each mouse and the mice were put into a pool to swim with load. The bath temperature was 25±2° C., and the depth was more than 30 cm. The survival time in the loaded swimming was recorded (when all parts of a mouse were under water for 10 s, the mouse was considered to be unable to rise to the surface). The results were shown in Table 10.1.

TABLE 10.1

Loaded swimming in model of normal mice

| Group | Survival time (min) |
|---|---|
| Blank control group | 13.51 ± 1.33 |
| Negative control group 1 | 13.45 ± 2.54 |
| Negative control group 2 | 12.54 ± 1.08 |
| Negative control group 3 | 12.97 ± 2.01 |
| Administration group 1 | 18.93 ± 2.13 |
| Administration group 2 | 15.35 ± 0.98 |
| Administration group 3 | 12.98 ± 3.04 |
| Administration group 4 | 17.01 ± 1.98 |
| Administration group 5 | 16.98 ± 2.35 |
| Administration group 6 | 17.23 ± 1.01 |
| Administration group 7 | 16.94 ± 1.68 |

The data in Table 10.1 indicated that the survival time in loaded swimming of mice in negative control groups 1 to 3 was equivalent to that in the blank control group, suggesting that the use of a single component from the present composition alone didn't lengthen the time in loaded swimming and had no effect on enhancing the physical stamina of the mice. Administration groups 1 to 2 and Administration groups 4 to 7 had a longer time in loaded swimming than the blank control group, and the difference was significant. That is, Compositions 1 to 2 and Compositions 4 to 7 were all capable of enhancing the physical stamina of mice so that they can swim with load for a longer time. The time in loaded swimming in administration group 3 was not different from that in the blank control group or negative control groups 1 to 3, suggesting that Composition 3 couldn't play a role in enhancing the physical stamina of mice or resisting fatigue because the content of the enzyme inhibitor was too low.

Administration groups 1 to 2 and Administration groups 4 to 7 had a longer time in loaded swimming than negative control groups 1 to 3, suggesting that Compositions 1 to 2 and Compositions 4 to 7 indeed can lengthen the time in loaded swimming and play a role in enhancing physical stamina and resisting fatigue. These compositions took effect 20 to 30 min after administration, achieving the efficacy of resisting fatigue.

In the comparison between administration group 1 and administration group 6, it can be easily found that administration group 1 involving trehalose provided a longer time in loaded swimming than administration group 6 involving the algal polysaccharide, showing that trehalose had a better effect on improvement of physical stamina and fatigue resistance than the algal polysaccharide although both substances were marine algae-derived materials. Meanwhile, the comparison between administration group 1 and administration groups 4 to 5 revealed that administration group 2 involving validamycin provided a longer time in loaded swimming than administration groups 4 to 5 involving hexaconazole and trehazolin respectively although all the three substances were enzyme inhibitors. The difference might be due to a better inhibitory effect of validamycin on the enzyme, and accordingly more marine algae-derived materials were absorbed into the small intestine so as to improve the physical stamina and resist fatigue. In contrast, as for Compositions 4 to 5 respectively containing hexaconazole and trehazolin, part of the trehaloses might be decomposed in the gastrointestinal tract, so the effect on fatigue resistance was inferior to that in administration group 1 involving administration of validamycin.

Data comparison among administration groups 1 to 3 indicated that with the increase of pbw (parts by weight) ratio of trehalose to validamycin, the effect on improvement of physical stamina and fatigue resistance was gradually reduced until zero. Such a fact suggested that with the decrease in concentration of the enzyme inhibitor, the ability of the composition to prevent the marine algae-derived material from being decomposed declined gradually so that the effect on improvement of physical stamina and fatigue resistance became worse and worse. When the pbw ratio of trehalose to validamycin reached 200000:1, the composition no longer had the effect on improvement of physical stamina and fatigue resistance, suggesting the percentage by mass occupied by the enzyme inhibitor cannot be lower than 0.001% in the composition of the present invention.

(II). Effect on Defecation Quantity in Normal Mice
1. Animals and Materials

Female ICR mice, 8 weeks old and 20±2 g in body weight, were purchased from Beijing HFK Bioscience Co., Ltd.

Composition solution: the solution of Composition 1 in this example was used.

2. Method

After the mice were fed normally for 3 days, they were randomly divided into three groups by body weight, i.e., a normal group, a control group and an administration group. The mice in the administration group were intragastrically given the solution of Composition 1 at a dose of 13.3 mL/kg body weight. The mice in the control group were intragastrically given sterile water for medical use at a dose of 13.3 mL/kg body weight while the mice in the normal group were normally raised. Twenty minutes after administration, the mice were put into a water bath to swim freely for 10 min. The bath temperature was 25±2° C. and the depth was greater than 30 cm. The eyeballs of the mice were excised to collect blood and the concentrations of urea and lactic acid in blood were determined by a biochemical analyzer. The results were shown in Table 10.2.

TABLE 10.2

Concentrations of urea and lactic acid in blood in model of normal mice

| Group | Concentration of urea in blood (mmol/L) | Concentration of lactic acid in blood (mmol/L) |
| --- | --- | --- |
| Normal group | 9.32 ± 0.98 | 7.36 ± 1.34 |
| Control group | 9.89 ± 1.07 | 7.88 ± 0.52 |
| Administration group | 6.96 ± 0.82 | 5.16 ± 0.81 |

The data in Table 10.2 indicated that the concentrations of urea and lactic acid in the administration group were both lower than those in the control group or the model group, and the differences were significant. That is, Composition 1 can significantly reduce the levels of urea and lactic acid in the blood of mice doing sports, enhancing physical stamina in mice so as to provide an effect on fatigue resistance.

(III). Human Experiment on Fatigue Resistance

1. Volunteer A, a female of 35 years old with a height of 160 cm and a body weight of 50 kg, was married with a child. Usually, she went to bed at 10 pm each night and had a good sleep. In this experiment, she took 200 mL of the solution of Composition 1 at about 10 pm and then surfed on Internet for entertainment till about 0:00. She didn't have obvious drowsiness and had a clear mind. She went to sleep at 1 am and could fall asleep normally. She got up at 7 am the next morning and went to work normally without a feeling of fatigue. During administration of this product, the subject didn't have any other discomforts.

2. Volunteer B, a male of 41 years old with a height of 170 cm and a body weight of 75 kg. He often stayed up late for work, but drinking coffee would cause palpitation. He took 200 mL of the solution of Composition 1 at 12 pm and then worked till 4 am next morning. During this period, he didn't have obvious drowsiness and had a clear mind. He got up at 6 am next morning and took the solution at the same dose. In this way, he took the solution for 3 days. During the administration period, he only slept for 1 to 3 h a day, but he could still work and hold meetings normally next day without any problems of drowsiness, dizziness and weakness. During the experiment, the subject didn't have any other discomforts.

3. Volunteer C, a male of 55 years old with a height of 180 cm and a body weight of 85 kg. He often took flights between China and United States and had to face the problem of jet lag. After he got off a plane at noon (a plane from China to United States), he took 200 mL of the solution of Composition 1. The flight fatigue was alleviated obviously, and he could work normally and the sleep at that night was not affected. This volunteer returned to regular schedule on the next day. The experiment results had proven the effect of Composition 1 on fatigue resistance. Such a composition can help people quickly regain strength, keep a clear mind and maintain a regular schedule. The composition of the present invention was not addictive. Its administration can be stopped at any time without adverse responses. People may take it according to need.

The experiments in the present examples indicated that the composition of the present invention had a prominent effect on reducing glucose, relaxing the bowels and purging the gut, losing weight, maintaining beauty and keeping young, ameliorating osteoporosis, improving sleeping, ameliorating menstrual disorder and resisting fatigue. It took effect fast and was safe without toxicity and side effects. It can be processed into various formulations for oral administration and tasted good. If it was in a form of pill, capsule or other solid oral formulations, patients may directly take it with water or beverage; if it was in a form of granule, solid beverage or powder, it may be dissolved in water or beverage before administration, or be directly taken with water or beverage; if it was an oral liquid, it may be directly taken or diluted with water or beverage before administration. It was convenient for patients.

INDUSTRIAL APPLICABILITY

The multi-functional composition in the present invention is of wide resources and low price. It provides no toxicity or side effects to human body. Further, it may be made into products in various oral forms and the production process is simple. It may applied for health-care and treatment with diabetes, constipation, obesity, calcium deficiency, insomnia and menstrual disorder in an industrial scale.

What is claimed is:

1. A multi-functional composition for oral administration or gastrointestinal administration comprising a marine algae-derived material and an enzyme inhibitor to an enzyme, the enzyme inhibitor comprising validamycin, hexaconazole, or trehazolin, the percentage by mass of the enzyme inhibitor in the multi-functional composition being no lower than 0.001% and no higher than 0.02%, the marine algae-derived material being one selected from the group consisting of algal saccharide extract, alginic acid, alginate, and a mixture thereof, the enzyme being one decomposing the marine algae-derived material in gastrointestinal tract, and the enzyme inhibitor being a substance preventing the enzyme from exerting decomposing effects.

2. The multi-functional composition of claim 1, wherein the algal saccharide extract is trehalose, other algal polysaccharide or a mixture thereof.

3. The multi-functional composition of claim 1, wherein the enzyme inhibitor further comprises 2R,5R-dimethylol-3R,4R-dihydroxy pyrrole, trehalostatin, Salbostatin, Suidatrestin, MDL25637, or a mixture thereof.

4. The multi-functional composition of claim 2, wherein the enzyme inhibitor further comprises 2R,5R-dimethylol-3R,4R-dihydroxy pyrrole, trehalostatin, Salbostatin, Suidatrestin, MDL25637, or a mixture thereof.

5. The multi-functional composition claim 1, wherein the alginate is one selected from the group consisting of sodium alginate, potassium alginate, calcium alginate and a mixture thereof.

6. The multi-functional composition of claim 2, wherein the alginate is one selected from the group consisting of sodium alginate, potassium alginate, calcium alginate and a mixture thereof.

7. A method for preparing the multi-functional composition of claim 1, wherein the multi-functional composition is a powder composition prepared by mixing a powdery marine algae-derived material and the enzyme inhibitor.

8. A method for preparing the multi-functional composition of claim 1, wherein the multi-functional composition is a liquid composition prepared by mixing a solution of the marine algae-derived material and a solution of the enzyme inhibitor or alternatively by dissolving a powder composition comprising the marine algae-derived material and the enzyme inhibitor.

9. The multi-functional composition of claim 1, wherein the marine algae-derived material is alginic acid.

10. The multi-functional composition of claim 1, wherein the algal saccharide extract further comprises other aquo compounds or isomers of the algal saccharide extract.

* * * * *